US009387230B2

(12) United States Patent
Dittmar et al.

(10) Patent No.: US 9,387,230 B2
(45) Date of Patent: Jul. 12, 2016

(54) METHODS TO TREAT CANCER USING CYCLOSPORINE AND CYCLOSPORINE DERIVATIVES

(71) Applicant: THE TRUSTEES OF COLUMBIA UNIVERSITY IN THE CITY OF NEW YORK, New York, NY (US)

(72) Inventors: John Dittmar, Leonia, NJ (US); Rodney J. Rothstein, Maplewood, NJ (US); Robert J. D. Reid, New York, NY (US); Ramon Parsons, Manhasset, NY (US); Matthew Maurer, New York, NY (US); Jacquelyn Shaw, Brooklyn, NY (US); Xing Du, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/057,780

(22) Filed: Oct. 18, 2013

(65) Prior Publication Data

US 2014/0154340 A1  Jun. 5, 2014

Related U.S. Application Data

(63) Continuation-in-part of application No. PCT/US2012/034118, filed on Apr. 18, 2012, which is a continuation-in-part of application No. PCT/US2012/034119, filed on Apr. 18, 2012.

(60) Provisional application No. 61/476,604, filed on Apr. 18, 2011.

(51) Int. Cl.
*A61K 38/13* (2006.01)
*A61P 35/00* (2006.01)
*A61K 45/06* (2006.01)
*A61K 31/501* (2006.01)
*A61K 38/12* (2006.01)

(52) U.S. Cl.
CPC .............. *A61K 38/13* (2013.01); *A61K 31/501* (2013.01); *A61K 38/12* (2013.01); *A61K 45/06* (2013.01)

(58) Field of Classification Search
CPC ..... A61K 38/13; A61K 45/06; A61K 31/501; A61K 38/12; A61K 2300/00
See application file for complete search history.

(56) References Cited

U.S. PATENT DOCUMENTS

| | | |
|---|---|---|
| 4,108,985 A | 8/1978 | Ruegger et al. |
| 4,220,641 A | 9/1980 | Traber et al. |
| 4,288,431 A | 9/1981 | Traber et al. |
| 4,384,996 A | 5/1983 | Bollinger et al. |
| 4,396,542 A | 8/1983 | Wenger |
| 4,554,351 A | 11/1985 | Wenger |
| 4,771,122 A | 9/1988 | Seebach |
| 4,798,823 A | 1/1989 | Witzel |
| 5,239,037 A | 8/1993 | Krishnan |
| 5,284,826 A | 2/1994 | Eberle |
| 5,293,057 A | 3/1994 | Ho et al. |
| 5,525,590 A | 6/1996 | Bollinger et al. |
| 5,595,756 A * | 1/1997 | Bally et al. .................... 424/450 |
| 7,468,419 B2 | 12/2008 | Wu et al. |
| 2002/0142946 A1 | 10/2002 | Or et al. |
| 2003/0087813 A1 | 5/2003 | Or et al. |
| 2003/0104992 A1 | 6/2003 | Or et al. |
| 2004/0106141 A1 | 6/2004 | Mischel et al. |
| 2006/0094646 A1 | 5/2006 | Clevenger |
| 2006/0094674 A1* | 5/2006 | Neel et al. ........................ 514/44 |
| 2006/0094676 A1 | 5/2006 | Lahav et al. |
| 2006/0106038 A1* | 5/2006 | Bouscary et al. ......... 514/263.21 |
| 2008/0206287 A1* | 8/2008 | Reed et al. ................. 424/277.1 |
| 2009/0221598 A1 | 9/2009 | Lin et al. |
| 2010/0152104 A1 | 6/2010 | Clevenger |
| 2010/0272722 A1 | 10/2010 | Feinstein et al. |

FOREIGN PATENT DOCUMENTS

| | | |
|---|---|---|
| EP | 34567 A2 | 8/1981 |
| EP | 56782 A1 | 7/1982 |
| EP | 300784 A2 | 1/1989 |
| EP | 300785 A2 | 1/1989 |
| GB | 2206119 A | 12/1988 |
| GB | 2207678 A | 2/1989 |
| WO | WO-86/02080 A1 | 4/1986 |
| WO | WO-99/18120 A1 | 4/1999 |
| WO | WO-03/033526 A2 | 4/2003 |
| WO | WO-2010/052559 A1 | 5/2010 |

OTHER PUBLICATIONS

Sporn, B and Suh, N, Chemoprevention of cancer, Carcinogenesis, 2000, 21, pp. 525-530.*
Auerbach. R. et al, Angiogenesis assays: Problems and pitfalls, Cancer and Metastasis Reviews, 2000, 19, pp. 167-172.*
Gura, T. Systems for Identifying New Drugs Are Often Faulty, Science, 1997, 278, pp. 1041-1042.*
Jain R. K., Barriers to Drug Delivery in Solid Tumors, Scientific American, 1994, pp. 58-65.*
Cancer Drug Design and Discovery. Neidle, Stephen, ed., Elsevier/ACademic Press, 2008, p. 427-431.*
Cellular and Molecular Basis of Cancer-Merck Manual, from http://www.merckmanuals.com/professional/print/hematology_and_oncology/overview_of . . . , pp. 1-5, accessed May 10, 2012.*
Lehmann et al, Identification of human triple-negative breast cancer subtypes and preclinical models for selection of targeted therapies, The Journal of Clinical Investigation, 2011, pp. 1-18.*

(Continued)

*Primary Examiner* — Julie Ha
*Assistant Examiner* — Li Ni Komatsu
(74) *Attorney, Agent, or Firm* — Wilmer Cutler Pickering Hale and Dorr LLP

(57) ABSTRACT

Methods to treat certain types of cancer with cyclophilin inhibitors.

15 Claims, 8 Drawing Sheets

(56) References Cited

OTHER PUBLICATIONS

Chalhoub et al, PTEN and the PI3-Kinase Pathway in Cancer, Annu. Rev. Pathol. Mech. Dis., 2009, 4, pp. 127-150.*
Koshy et al, Cisplatin-gemcitabine therapy in metastatic breast cancer: Improved outcome in triple negative breast cancer patients compared to non-triple negative patients, The Breast, 2010, 19, pp. 246-248, published online Mar. 15, 2010.*
Mitomycin C, from http://pubchem.ncbi.nlm.nih.gov/rest/chemical/mitomycin, p. 1, accessed Oct. 10, 2014.*
American Cancer Society, Inc., "Cancer Facts and Figures 2010," 68 pages (2010).
Bachovchin, D. A. et al., "Substrate-Free High-Throughput Screening Identifies Selective Inhibitors for Uncharacterized Enzymes," Nat. Biotechnol., vol. 27, No. 4, pp. 387-394, 18 pages (Apr. 2009).
Bartz, S. R. et al., "Inhibition of human immunodeficiency virus replication by nonimmunosuppressive analogs of cyclosporin A," Proc. Natl. Acad. Sci. USA, vol. 92, No. 12, pp. 5381-5385 (Jun. 6, 1995).
Bennett, C. B. et al., "Yeast screens identify the RNA polymerase II CTD and SPT5 as relevant targets of BRCA1 interaction," PLoS One, vol. 3, No. 1, e1448, pp. 1-15 (Jan. 2008).
Bryant, H. E. et al., "Specific killing of BRCA2-deficient tumours with inhibitors of poly(Adp-ribose) polymerase," Nature, vol. 434, No. 7035, pp. 913-917, 6 pages (Apr. 14, 2005).
Cantley, L. C., "The phosphoinositide 3-kinase pathway," Science, vol. 296, No. 5573, pp. 1655-1657 (May 31, 2002).
Chambers, S. K. et al., "Phase I trial of intravenous carboplatin and cyclosporin a in refractory gynecologic cancer patients," Clinical Cancer Research, vol. 2, No. 10, pp. 1699-1704 (Oct. 1996).
Ciechomska, I. et al., "Cyclosporine A and its non-immunosuppressive derivative NIM811 induce apoptosis of malignant melanoma cells in vitro and in vivo studies," Int. J. Cancer, vol. 117, No. 1, pp. 59-67 (Oct. 20, 2005).
Collins, S. R. et al., "Functional dissection of protein complexes involved in yeast chromosome biology using a genetic interaction map," Nature, vol. 446, No. 7137, pp. 806-810 (Apr. 12, 2007).
Costanzo, M. et al., "The genetic landscape of a cell," Science, vol. 327, No. 5964, pp. 425-431 (Jan. 22, 2010).
Cruz, M. C. et al., "Immunosuppressive and nonimmunosuppressive cyclosporine analogs are toxic to the opportunistic fungal pathogen Cryptococcus neoformans via cyclophilin-dependent inhibition of calcineurin," Antimicrobial Agents and Chemotherapy, vol. 44, No. 1, pp. 143-149 (Jan. 2000).
Dedes, K. J. et al., "PTEN Deficiency in Endometrioid Endometrial Adenocarcinomas Predicts Sensitivity to PARP Inhibitors," Sci. Transl. Med., vol. 2, pp. 1-8 (Oct. 13, 2010).
Dittmar, J. C. et al., "ScreenMill: A freely available software suite for growth measurement, analysis and visualization of high-throughput screen data," BMC Bioinformatics, vol. 11, No. 353, pp. 1-11 (2010).
Dowling, R. J. et al., "Metformin inhibits mammalian target of rapamycin-dependent translation initiation in breast cancer cells," Cancer Res., vol. 67, No. 22, pp. 10804-10812 (Nov. 15, 2007).
Duan, R. F. et al., "Proteomic Analysis of Two Strains of MEF Cells with Pten Deletion," Molecular & Cellular Proteomics, vol. 3, Suppl. 10, pp. S36- (2004), Abstract only.
Engelman, J. A. et al., "The evolution of phosphatidylinositol 3-kinases as regulators of growth and metabolism," Nat. Rev. Genet., vol. 7, No. 8, pp. 606-619 (Aug. 2006).
Farmer, H. et al., "Targeting the DNA repair defect in BRCA mutant cells as a therapeutic strategy," Nature, vol. 434, No. 7035, pp. 917-921 (Apr. 14, 2005).
Fisher, G. A. et al., "Pharmacological considerations in the modulation of multidrug resistance," Eur. J. Cancer, vol. 32A, No. 6, pp. 1082-1088 (Jun. 1996).
Giorgini, F. et al., "A genomic screen in yeast implicates kynurenine 3-monooxygenase as a therapeutic target for Huntington disease," Nat. Genet., vol. 37, No. 5, pp. 526-531, 13 pages (May 2005).
Gregory, M. A. et al., "Preclinical characterisation of naturally occurring polyketide cyclophilin inhibitors from the sanglifehrin family," Antimicrob. Agents Chemother., vol. 55, No. 5, pp. 1975-1981 (May 2011).
Han, X. et al., "Cyclosporin A and sanglifehrin A enhance chemotherapeutic effect of cisplatin in C6 glioma cells," Oncology Reports, vol. 23, No. 4, pp. 1053-1062 (Apr. 2010).
He, Y. et al., "N-benzyladriamycin-14-valerate (AD198) induces apoptosis through protein kinase C-delta-induced phosphorylation of phospholipid scramblase 3," Cancer Res., vol. 65, No. 21, pp. 10016-10023 (Nov. 1, 2005).
Heinicke, S. et al., "The Princeton Protein Orthology Database (P-POD): a comparative genomics analysis tool for biologists," PLoS One, vol. 2, No. 8, e766, pp. 1-15 (Aug. 22, 2007).
Hopkins, S. et al., "SCY-635, a Novel Nonimmunosuppressive Analog of Cyclosporine That Exhibits Potent Inhibition of Hepatitis C Virus RNA Replication In Vitro," Antimicrob. Agents Chemother., vol. 54, No. 2, pp. 660-672 (Feb. 2010).
Hsu, V. L. and Armitage, I. M., "Solution structure of cyclosporin A and a nonimmunosuppressive analog bound to fully deuterated cyclophilin," Biochemistry, vol. 31, No. 51, pp. 12778-12784 (Dec. 29, 1992).
International Search Report and Written Opinion issued by the U.S. Patent and Trademark Office as International Searching Authority for Application No. PCT/US2012/034118 dated Jul. 24, 2012 (9 pages).
Kallen, J. et al., "X-ray structures and analysis of 11 cyclosporin derivatives complexed with cyclophilin A," J. Mol. Biol., vol. 283, No. 2, pp. 435-449 (Oct. 23, 1998).
Keller, R. P. et al., "SDZ PSC 833, A non-immunosuppressive cyclosporine: Its potency in overcoming P-glycoprotein-mediated multidrug resistance of murine leukemia," International Journal of Cancer, vol. 50, No. 4, pp. 593-597 (Feb. 20, 1992).
Khurana, V. and Lindquist, S., "Modelling neurodegeneration in *Saccharomyces cerevisiae*: why cook with baker's yeast?," Nat. Rev. Neurosci., vol. 11, No. 6, pp. 436-449 ( Jun. 2010).
Kim, J. et al., "Centrosomal PKCBII and pericentrin are critical for human prostate cancer growth and angiogenesis," Cancer Res., vol. 68, No. 16, pp. 6831-6839, 22 pages (Aug. 15, 2008).
Kobel, H. and Traber, R., "Directed Biosynthesis of Cyclosporins," European J. Applied Microbiology and Biotechnology, vol. 14, pp. 237-240 (1982).
Kohjima, M. et al., "NIM811, a nonimmunosuppressive cyclosporine analogue, suppresses collagen production and enhances collagenase activity in hepatic stellate cells," Liver Int., vol. 27, No. 9, pp. 1273-1281 (Nov. 2007).
Kraus, M. H. et al., "Overexpression of the EGF receptor-related proto-oncogene erbB-2 in human mammary tumor cell lines by different molecular mechanisms," Embo J., vol. 6, No. 3, pp. 605-610 (Mar. 1987).
Kroll, E. S. et al., "Establishing genetic interactions by a synthetic dosage lethality phenotype," Genetics, vol. 143, No. 1, pp. 95-102 (May 1996).
Liu, X. et al., "Inhibition of the phosphatidylinositol 3-kinase/Akt pathway sensitizes MDA-MB468 human breast cancer cells to cerulenin-induced apoptosis," Molecular Cancer Therapeutics, vol. 5, No. 3, pp. 494-501 (Mar. 2006).
Lopez-Ramos, M. et al., "New potent dual inhibitors of CK2 and Pim kinases: discovery and structural insights," FASEB J., vol. 24, No. 9, pp. 3171-3185 (Sep. 2010).
Ma, S. et al., "NIM811, a Cyclophilin Inhibitor, Exhibits Potent In Vitro Activity against Hepatitis C Virus Alone or in Combination with Alpha Interferon," Antimicrobial Agents and Chemotherapy, vol. 50, No. 9, pp. 2976-2982 (Sep. 2006).
McGuire, J. J. et al., "Potent inhibition of human folylpolyglutamate synthetase by a phosphinic acid mimic of the tetrahedral reaction intermediate," Biochem. Pharmacol., vol. 65, No. 3, pp. 315-318 (Feb. 1, 2003).
Measday, V. and Hieter, P., "Synthetic dosage lethality," Methods Enzymol., vol. 350, pp. 316-326 (2002).
Measday, V. et al., "Ctf3p, the Mis6 budding yeast homolog, interacts with Mcm22p and Mcm16p at the yeast outer kinetochore," Genes Dev., vol. 16, No. 1, pp. 101-113 (Jan. 1, 2002).
Mendes-Pereira, A. M. et al., "Synthetic lethal targeting of PTEN mutant cells with PARP inhibitors," EMBO Mol. Med., vol. 1, No. 6-7, pp. 315-322 (Sep. 2009).

(56) References Cited

OTHER PUBLICATIONS

Michlewski, G. et al., "The splicing factor SF42/ASF regulates translation initiation by enhancing phosphorylation of 4E-BP1," Mol. Cell, vol. 30, No. 2, pp. 179-189 (Apr. 25, 2008).

Morgan, R. J. Jr. et al., "Phase II trial of carboplatin and infusional cyclosporine with alpha-interferon in recurrent ovarian cancer: a California Cancer Consortium Trial," Int. J. Gynecol. Cancer, vol. 17, No. 2, pp. 373-378 (Mar.-Apr. 2007).

Neben, K. et al., "Gene expression patterns in acute myeloid leukemia correlate with centrosome aberrations and numerical chromosome changes," Oncogene, vol. 23, No. 13, pp. 2379-2384 (Mar. 25, 2004).

Paeshuyse, J. et al., "The non-immunosuppressive cyclosporin DEBIO-025 is a potent inhibitor of hepatitis C virus replication in vitro," Hepatology, vol. 43, No. 4, pp. 761-770 (Apr. 2006).

Park, S. B. and Meier, G. P., "A semi-synthetic approach to olefinic analogs of amino acid one (MeBMT) in cyclosporin A," Tetrahedron Letters, vol. 30, No. 32, pp. 4215-4218 (1989).

Piaggi, S. et al., "Glutathione transferase omega 1-1 (GSTO1-1) plays an anti-apoptotic role in cell resistance to cisplatin toxicity," Carcinogenesis, vol. 31, No. 5, pp. 804-811 (May 2010).

Podsypanina, K. et al., "An inhibitor of mTOR reduces neoplasia and normalizes p70/S6 kinase activity in Pten+/−mice," Proc. Natl. Acad. Sci. USA, vol. 98, No. 18, pp. 10320-10325 (Aug. 28, 2001).

Racanelli, A. C. et al., "Therapeutics by cytotoxic metabolite accumulation: pemetrexed causes ZMP accumulation, AMPK activation, and mammalian target of rapamycin inhibition," Cancer Res., vol. 69, No. 13, pp. 5467-5474, 16 pages (Jul. 1, 2009).

Reid, R. J. D. et al., "Selective ploidy ablation, a high-throughput plasmid transfer protocol, identifies new genes affecting topoisomerase I-induced DNA damage," Genome Research, vol. 21, No. 3, pp. 477-486 (Mar. 2011).

Saal, L. H. et al., "PIK3CA mutations correlate with hormone receptors, node metastasis, and ERBB2, and are mutually exclusive with PTEN loss in human breast carcinoma," Cancer Res., vol. 65, No. 7, pp. 2554-2559 (Apr. 1, 2005).

Saal, L. H. et al., "Poor prognosis in carcinoma is associated with a gene expression signature of aberrant PTEN tumor suppressor pathway activity," Proc. Natl. Acad. Sci. USA, vol. 104, No. 18, pp. 7564-7569 (May 1, 2007).

Salmena, L. et al., "Tenets of PTEN tumor suppression," Cell, vol. 133, No. 3, pp. 403-414 (May 2, 2008).

Samuels, Y. and Ericson, K., "Oncogenic PI3K and its role in cancer," Curr. Opin. Oncol., vol. 18, No. 1, pp. 77-82 (Jan. 2006).

Slamon, D. J. et al., "Human breast cancer: correlation of relapse and survival with amplification of the HER-2/neu oncogene," Science, vol. 235, No. 4785, pp. 177-182 (Jan. 9, 1987).

Tong, A. H. et al., "Global mapping of the yeast genetic interaction network," Science, vol. 303, No. 5659, pp. 808-813 (Feb. 6, 2004).

von Traber, R., et al. "Isolation and structure determination of the new cyclosporins E, F, G, H und I," Helvetica Chimica Acta, vol. 65, No. 5, pp. 1655-1677 (1982), Summary only.

von Traber, R. et al., "The structure of cyclosporine C," Helvetica Chimica Acta, vol. 60, No. 4, pp. 1247-1255 (1977), Summary only.

von Wartburg, A. and Traber, R., "Chemistry of the natural cyclosporin metabolites," Progress in Allergy, vol. 38, pp. 28-45 (1986).

Wenger, Roland Maurice, "Synthesis of Cyclosporine and Analogues: Structural Requirements for Immunosuppressive Activity," Angewandte Chemie International Edition in English, vol. 24, No. 2, pp. 77-85 (Feb. 1985).

Wenger, Roland Maurice, "Cyclosporine and Analogues—Isolation and Synthesis—Mechanism of Action and Structural Requirements for Pharmacological Activity," Progress in the Chemistry of Organic Natural Products, vol. 50, pp. 123-168 (1986).

Wenger, Roland, "Synthesis of Cyclosporine and Analogues: Structure, Activity, Relationships of New Cyclosporine Derivatives," Transplantation Proceedings, vol. XV, No. 4, Suppl. 1, pp. 2230-2241 (Dec. 1983).

Willingham, S. et al., "Yeast genes that enhance the toxicity of a mutant huntingtin fragment or alpha-synuclein," Science, vol. 302, No. 5651, pp. 1769-1772 (Dec. 5, 2003).

Wong, K.K. et al., "Targeting the PI3K signaling pathway in cancer," Curr. Opin. Genet. Dev., vol. 20, No. 1, pp. 87-90, 7 pages (Dec. 11, 2009).

Zenke, G. et al., "Sanglifehrin A, a Novel Cyclophilin-Binding Compound Showing Immunosuppressive Activity with a New Mechanism of Action," The Journal of Immunology, vol. 166, No. 12, pp. 7165-7171 (Jun. 15, 2001).

Zhou, G. et al., "Role of AMP-activated protein kinase in mechanism of metformin action," J. Clin. Invest., vol. 108, No. 8, pp. 1167-1174 (Oct. 2001).

International Search Report and Written Opinion mailed on Sep. 18, 2012 for related PCT Application No. PCT/US2012/034119; 18 pages.

* cited by examiner

Ra = Rb = H      Cyclosporin A

Ra = H   Rb = OH      211-810

Ra = SMe  Rb = H      209-825

US 9,387,230 B2

METHODS TO TREAT CANCER USING CYCLOSPORINE AND CYCLOSPORINE DERIVATIVES

CROSS REFERENCE TO RELATED APPLICATIONS

This application is a continuation-in-part of International Application Nos. PCT/US12/34118, filed Apr. 18, 2012 and PCT/US12/34119, filed Apr. 18, 2012, each of which claims the benefit of U.S. Ser. No. 61/476,604, filed Apr. 18, 2011, the content of each of these applications is hereby incorporated by reference in its entirety.

The contents of all patents, patent applications and non-patent references listed in the specification are incorporated by reference herewith.

STATEMENT REGARDING FEDERALLY SPONSORED RESEARCH OR DEVELOPMENT

This invention was made with government support under CA125520 and CA013696 awarded by NCI-NIH. The government has certain rights in the invention.

BACKGROUND

Breast Cancer is one of the major cancers affecting women with an estimated 200,000 new cases of invasive breast cancer in the US during 2010[1]. Although mortality rates have declined over the past decade, this disease still accounts for nearly 40,000 deaths annually[1]. PTEN deficient breast cancers show poor prognosis with a high rate of metastasis to distant organs. An important barrier to progress in treating this disease is the lack of effective drugs that attack cancer cells without harming the surrounding normal tissue. Cancer treatments that target differences in the molecular makeup of cancer cells show great promise, but these therapies are often limited because the molecular target is not uniformly present in an affected population. For example some breast cancers can be treated with herceptin, but this drug is only effective in the 15-20% of breast cancers that show amplification of HER2[2,3]. An important approach to overcoming such an obstacle is to define additional therapeutic targets to treat a broader set of the affected population, either alone or in combination with existing treatments.

SUMMARY

The inventors screened yeast using an over-expression system that they designed specifically to identify genetic interactions with over-expression of genes associated with cancers, for example, but not limited to, PTEN-deficient breast cancer. Among the target genes that the inventors identified is yeast cyclophilin (CPR1), the orthologue of human CPYA, peptidyl-prolyl cis-trans isomerase, a target of cyclosporin. The inventors tested cancer cell lines, for example, but not limited to, PTEN deficient cancer cell lines, for sensitivity to cyclosporin, and found a 10-fold increased sensitivity to the drug cyclosporine.

In certain aspects, the invention provides a method to treat cancer in a subject in need of treatment therefor, the method comprising: contacting a PTEN negative cancer in a subject in need of treatment with a therapeutic amount of a cyclosporine, whereby the cancer is treated.

In certain aspects, the invention provides a method to reduce growth of a cancer cell in a subject in need of treatment therefor, the method comprising: contacting a PTEN negative cancer cell in a subject in need of treatment with a therapeutic amount of a cyclosporine, whereby the growth of the cancer is reduced compared to PTEN positive cancer cells.

In certain aspects, the invention provides a method to induce apoptosis of a cancer cell in a subject in need of treatment therefor, the method comprising: contacting a PTEN negative cancer cell in a subject in need of treatment with a therapeutic amount of a cyclosporine, whereby apoptosis of the cancer cell is induced and the subject is treated.

In certain aspects, the invention provides a method to treat cancer in a subject in need of treatment therefor, the method comprising: administering to a subject diagnosed with a PTEN negative cancer a therapeutic amount of a cyclosporine, whereby the cancer is treated.

In non-limiting embodiments, the cyclosporine may be selected among a number of naturally occurring cyclosporin molecules. A non-limiting example of such naturally occurring molecule is cyclosporine A. In other embodiments, the cyclosporine may be a cyclosporine derivative. In other embodiments, the cyclosporine derivative is a non-immunosuppressive derivative.

In certain aspects, the invention provides a method to treat cancer in a subject in need of treatment therefor, the method comprising: contacting a PTEN negative cancer in a subject in need thereof with a therapeutic amount of sanglifehrin, whereby the cancer is treated.

In certain aspects, the invention provides a method to reduce growth of a cancer cell in a subject in need thereof, the method comprising: contacting a PTEN negative cancer cell in a subject in need of treatment therefor with a therapeutic amount of sanglifehrin, whereby the growth of the cancer is reduced compared to PTEN positive cancer cells.

In certain aspects, the invention provides a method to induce apoptosis of a cancer cell in a subject in need thereof, the method comprising: contacting a PTEN negative cancer cell in a subject in need thereof with a therapeutic amount of sanglifehrin, whereby apoptosis of the cancer cell is induced and the subject is treated.

In certain aspects, the invention provides a method to treat cancer in a subject in need of treatment therefor, the method comprising: administering to a subject diagnosed with a PTEN negative cancer a therapeutic amount of sanglifehrin, whereby the cancer is treated.

In certain embodiments, the cancer is PTEN negative cancer. In non-limiting embodiments, the PTEN negative cancer is breast cancer, prostate cancer, colon cancer, glioblastoma, endometrial cancer, lung cancer, thyroid cancer, lymphomas, ovarian cancer, or a combination thereof. In non-limiting embodiments the breast cancer is a triple negative breast cancer. In non-limiting embodiments, the prostate cancer is a hormone negative prostate cancer.

In certain aspects the invention provides a method to treat a PTEN negative cancer in a subject in need of treatment therefor, the method comprising: contacting the PTEN negative cancer in the subject in need of treatment therefor with a therapeutic amount of an agent which inhibits cyclophilin activity, whereby the cancer is treated. In certain aspects the invention provides a method to reduce growth of a PTEN negative cancer cell in a subject in need thereof, the method comprising: contacting the PTEN negative cancer cell in the subject in need thereof with a therapeutic amount of an agent which inhibits cyclophilin activity, whereby the growth of the cancer is reduced or inhibited compared to PTEN positive cancer cells. In certain aspects the invention provides a method to induce apoptosis of a PTEN negative cancer cell in a subject in need thereof, the method comprising: contacting the PTEN negative cancer cell in the subject in need of treatment therefor with a therapeutic amount of an agent which inhibits cyclophilin activity, whereby apoptosis of the cancer cell is induced and the subject is treated. In certain aspects the invention provides a method to treat cancer in a subject suffering from a PTEN negative cancer, the method comprising: administering to the subject suffering from a PTEN negative cancer a therapeutic amount of an agent which inhibits cyclophilin activity, whereby the cancer is treated.

In certain aspects the invention provides a method to treat cancer in a subject in need of treatment therefor, the method comprising: contacting an SFRS1 or pericentrin overexpressing cancer in a subject in need of treatment therefor with a therapeutic amount of an agent which inhibits cyclophilin activity, whereby the cancer is treated. In certain aspects the invention provides a method to reduce growth of a cancer cell in a subject in need thereof, the method comprising: contacting an SFRS1 or pericentrin overexpressing cancer cell in a subject in need of treatment therefor with a therapeutic amount of an agent which inhibits cyclophilin activity, whereby the growth of the cancer is reduced. In certain aspects the invention provides a method to treat cancer in a subject, the method comprising: administering to a subject suffering from an SFRS1 or pericentrin overexpressing cancer a therapeutic amount of an agent which inhibits cyclophilin activity, whereby the cancer is treated. In certain non-limiting embodiments, the cancer is an ovarian neoplasia. In certain non-limiting embodiments, the cyclophilin inhibitor is a cyclosporine derivative which is non-immunosuppressive.

In certain embodiments, the methods of the invention consist essentially of contacting a cancer cell in a subject in need of treatment therefor with a therapeutic amount of an agent which inhibits cyclophilin activity, whereby the growth of the cancer cell is inhibited or reduced. In certain embodiments, the methods of the invention consist of contacting a cancer cell in a subject in need of treatment therefor with a therapeutic amount of an agent which inhibits cyclophilin activity, whereby the growth of the cancer cell is inhibited or reduced. In certain embodiments, the methods of the invention consist essentially of administering to a subject in need thereof a therapeutic amount of an agent which inhibits cyclophilin activity, whereby the growth of the cancer cell is inhibited or reduced. In certain embodiments, the methods of the invention consist of administering to a subject in need thereof a therapeutic amount of an agent which inhibits cyclophilin activity, whereby the growth of the cancer cell is inhibited or reduced.

Non-limiting examples of agents used as cyclophilin inhibitors include naturally occurring cyclosporines, cyclosporine derivatives, sanglifehrins, for example, but not limited to, sanglifehrins A-D, or any combination thereof. In non-limiting embodiments of the methods, the cyclosporine is a naturally occurring cyclosporine, for example, but not limited to, cyclosporine A. In non-limiting embodiments of the methods, the cyclosporine derivative is a non-immunosuppressive cyclosporine derivative. In non-limiting embodiments of the methods, the cyclosporine derivative is the agent of Formula I, the agent of Formula II, NIM-811, SCY-635, DEBIO-025, Formula III, Formula IV, Formula V, Formula VI, Formula VII, Formula VIII, or any combination thereof. In non-limiting embodiments of the methods, the sanglifehrin is sanglifehrinA, sanglifehrinB, sanglifehrinC, sanglifehrinD, or any combination thereof.

In certain embodiments of the methods, the therapeutic amount of cyclosporine or cyclosporine derivative is administered in a combination with a therapeutic amount of a PARP inhibitor or a DNA cross-linking agent, or a combination thereof.

In certain embodiments of the methods, the therapeutic amount of sanglifehrin is administered in a combination with a therapeutic amount of a PARP inhibitor or a DNA cross-linking agent, or a combination thereof.

In certain embodiments of the methods, the DNA cross-linking agent is cisplatin, mitomycin C, cyclophosphamide, chlorambucil, uramustine, ifosfamide, melphalan, bendamustine, carmustine, or any combination thereof.

In certain embodiments of the methods, the PARP inhibitor is olaparib.

Non-limiting examples of PTEN negative cancers include breast cancer, prostate cancer, colon cancer, glioblastoma, endometrial cancer, lung cancer, thyroid cancer, lymphomas, ovarian cancer, and combinations thereof.

BRIEF DESCRIPTION OF THE DRAWINGS

FIG. 1A shows percent growth inhibition for MCF10A Parental vs. PTEN null. FIG. 1B shows percent growth inhibition for MCF10A Double vs. Triple Modified. FIG. 1C shows percent growth inhibition for HTC 116 wild type vs. PTEN null. Proliferation of three isogenic cancer cell lines using CsA. Cells were plated in 48 well plates and treated with drug for ten days before quantifying cell proliferation using crystal violet assays.

(96) hours after treatment, the cells were stained with crystal violet for cell growth. The cell growth of negative control group is set as 100%.

FIGS. 9A-9D show MCF10A wild type (WT) and PTEN knockout (PT−/−) cells were seeded into 48-well plate with a density of 4000 cells/well. The next day, the growth medium was changed to a medium containing CsA (FIG. 9A) or an analog as depicted in each panel in FIG. 9B-D. Medium containing 0.1% DMSO was used as negative control. Ninety-six (96) hours after treatment, the cells were stained with crystal violet for cell growth. The cell growth of negative control group is set as 100%. Formula III is 8T2. Formula IV is RLY-001. Formula V is RLY-018. Formula VI is RLY-045. Formula VII is RLY-062. Formula VIII is RLY-070.

Figure 10A:
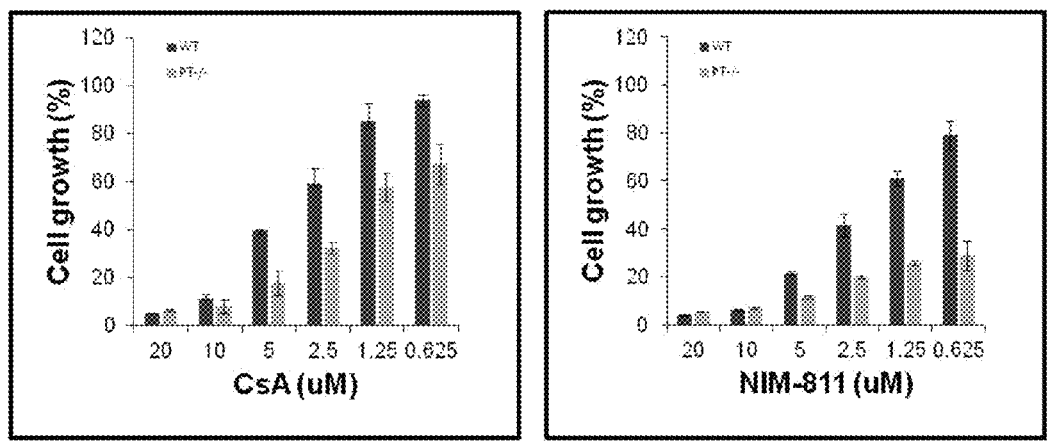

FIG. 10A shows the results for MCF10A wild type (WT) and PTEN knockout (PT−/−) cells seeded into 48-well plates at a density of 4000 cells/well. The next day, the growth medium was changed to a medium containing Cyclosporine A (CsA) and the non-immunosuppressive Cyclosporine analog, NIM-811. Medium containing 0.1% DMSO was used as negative control. Ninety-six (96) hours after treatment, the cells were stained with crystal violet and measured for cell growth. Cell growth of the negative control group is set as 100%.

Figure 10B:
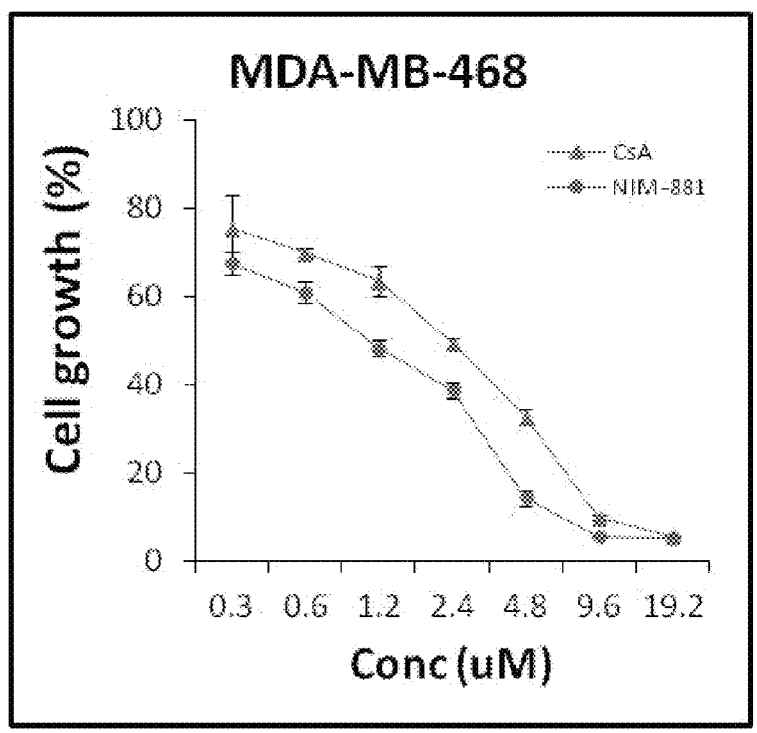

FIG. 10B shows the results for MDA-MB-468 cells (PT−/−) seeded into 48-well plates at a density of 5000 cells/well. The next day, the growth medium was changed to medium containing CsA and NIM-811. Medium containing 0.1% DMSO was used as negative control. The medium was replenished once. Seven days after treatment, the cells were stained with crystal violet and measured for cell growth. Cell growth of the negative control group is set as 100%.

DETAILED DESCRIPTION

Figure 7:
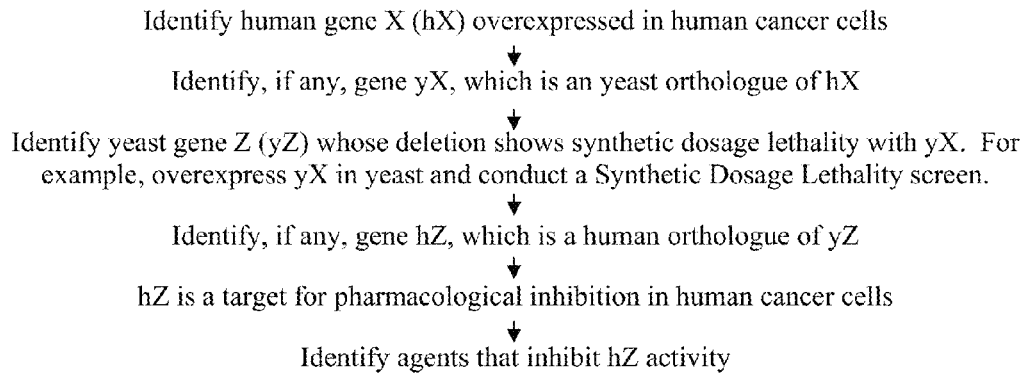
FIG. 7 shows a schematic representation of the method to identify human genes as pharmacological targets for inhibition in cancer cells, based on a synthetic dosage lethality screen in yeast.

The invention provides methods to identify genetic targets for pharmacological inhibition by defining synthetic genetic interactions that are specific to cancer cells (FIG. 7). This type of treatment shows great promise. For example, therapies are being developed to exploit the synthetic lethal interaction between BRCA1/BRCA2 and PARP. Since many breast cancers are BRCA1 or BRCA2 deficient, inhibiting PARP leads to cancer cell-specific death[4,5].

PI3K pathway in breast cancer. The PI3K pathway is perhaps the most important intracellular pathway activated in cancer[7]. Mutations of core pathway components (PTEN, PIK3CA) occur in a large subset of adult-onset cancers of the breast, prostate, colon, uterus, brain, and skin. Activation of the PI3K pathway by mutation of PTEN and PIK3CA in model systems leads to cardinal features of cancer, including cell proliferation, genetic instability, cell survival, migration, and angiogenesis to generate full blown malignancy[8]. Inhibiting the PI3K pathway has been shown to have a therapeutic effect in multiple cancer models[7,9]. In addition, the PI3K pathway is critical for regulation of cellular proliferation, size, branching, migration, metabolism, oxidative stress, survival, and autophagy[10-12]. Approximately half of all breast cancers have alterations leading to activation of the AKT pathway[13]. Such pathway activation is associated with a subset of breast cancers with a predisposition for metastasis to distant organs and poor prognosis for patients with such tumors. We have recently performed gene expression profiling on 105 stage II breast tumors that were typed for PTEN expression by immunohistochemistry[6].

Gene expression profiles that were significantly different in PTEN-deficient vs. PTEN-normal breast cancer cells were aggregated into a "signature" set that is enriched for cell cycle genes. The signature gene expression profile contains genes that are up-, or down-regulated in the PTEN-deficient tumors and are predictive of poor prognosis. Many of the genes showing expression changes in the PTEN-deficient tumors have clear orthologs in the yeast *Saccharomyces cerevisiae* (Table 1). This gene expression data was used to undertake a search for genetic interactions—such as synthetic lethality (SL)—that can be exploited for cancer therapy. We also searched for a different kind of synthetic genetic interaction, namely synthetic dosage lethality (SDL), which results when over-expression of one gene causes lethality only when another gene is deleted[14-16]. In this case, SDL genetic interactions identify potential target genes that are not essential on their own, but become essential when, for example, one of the genes identified from the PTEN signature is over-expressed. This approach is novel and has provided new gene targets to attack this particularly aggressive form of breast cancer.

*Saccharomyces* as a model for human disease. Approximately 60% of yeast genes have either a direct human ortholog or at least one domain that is conserved in a human gene[17]. Given the human-yeast orthology, recent studies have been performed to identify conserved genetic interactions in yeast that are relevant to Huntington's disease and BRCA1 expression in breast cancer[19-21]. Such studies are facilitated by an extensive set of resources. The establishment of a gene disruption library has fostered the development of high throughput protocols that cover the complete *Saccharomyces* genome. Comprehensive SL genetic screens are ongoing in several labs[22-24]. SDL interactions were first described in yeast, and we developed a high throughput method to perform these screens as described herein below. Thus performing these screens in yeast provides an extremely rapid and efficient system in which to identify genetic interactions for both increased and decreased gene expression. These genetic interactions were validated in PTEN-deficient tumor cells using RNAi methods to confirm the yeast results. In addition, the vast amount of genetic information that has become available from our yeast screens as well as from those of others, has helped define pathways that become essential upon over-expression of genes or sets of genes that are downstream of the AKT pathway.

TABLE 1

Human genes from the PTEN-deficient signature set and their yeast orthologs identified using the Princeton Orthology Database (18). In case of orthology with a gene family, all yeast members are listed. Asterisk indicates that Pericentrin is not part of the PTEN signature.

| human gene over-expressed | Yeast ortholog |
| --- | --- |
| ATAD2 | YTA7 |
| BUB1 | BUB1 |
| CDC7 | CDC7 |
| CHAF1B | CAC2 |
| CKS2 | CKS1 |
| MCM3 | MCM3 |
| MCM6 | MCM6 |
| PCNA | POL30 |
| PTTG1 | PDS1 |
| SENP5 | ULP1 ULP2 |
| SFRS1 | NPL3 |
| SGOL2 | SGO1 |
| STK6 | IPL1 |
| TOPBP1 | DPB11 |
| KPNA2 | SRP1 |
| STIP1 | ST11 |
| PSMD12 | RPN5 |
| RAD51C | RAD57 DMC1 |
| Pericentrin* | SPC110 |

Yeast methods to identify SL interactions are well established[23,24], and these screens are performed using known methods. We focused on defining synthetic dosage lethal interactions (SDLs). This type of lethal genetic interaction occurs when a gene becomes essential only when a second gene is over-expressed[14,16]. Identifying these interactions is important with respect to the PTEN-deficient breast cancers as approximately ⅔ of the gene expression changes in the PTEN-signature are increases. We developed a high throughput method to screen for SDLs with any query gene. This method makes use of a 'donor' strain in which the whole set of 16 donor chromosomes can be destabilized and lost. Plasmids carried in this donor strain are transferred to a new strain by mating, followed by destabilization and counter-selection of all the donor chromosomes producing a recipient haploid containing the plasmid. We refer to this procedure as selective ploidy ablation (SPA). The SPA process is efficient and allows plasmids to be transferred to multiple haploid strains by replica pinning in a 6 day procedure. A manuscript describing this procedure is published. See Genome Research 21: 477-486, 2011.

To quantify results from the SPA screens, we developed a software suite to automate measurement of colony growth using scanned images of the screen plates. The software performs normalization routines to correct for any plate-specific growth defects, compares experimental to control conditions and calculates statistics. A manuscript describing this software has been published in *BMC Bioinformatics*. See BMC Bioinformatics 11: 353-, 2010.

We have performed SDL screens for the 21 yeast genes, corresponding to the 19 mammalian homologues, listed in Table 1. Twenty of these genes are overexpressed in the PTEN-deficient signature from Saal et al. (6). Expression of Pericentrin is correlated with chromosomal abnormalities in myeloid leukemia and prostate cancers. See Neben, K., Tews, B., Wrobel, G., Hahn, M., Kokocinski, F., Giesecke, C., Krause, U., Ho, A. D., Kramer, A., Lichter, P., Gene expression patterns in acute myeloid leukemia correlate with centrosome aberrations and numerical chromosome changes. Oncogene 23 (13) 2379-84 (2004)); Kim J, Choi Y, Vallentin A, Hunrichs B S, Hellerstein M K, Peehl D M, Mochly-Rosen D., Centrosomal PKCβII and pericentrin are critical for human prostate cancer growth and angiogenesis. Cancer Res. 68 (16) 6831-39 (2008). We find a substantial overlap among the genes isolated in the separate screens. For example, there are 100 deletion strains that are common to 6 or more SDL screens and 300 that are common to 4 or more SDL screens. For instance, expression of NPL3 (SFRS1) in every haploid strain in the yeast gene disruption library identifies a number of genes affecting the DNA damage checkpoint response (such as CTF8 and CTF18) or the spindle assembly checkpoint (BUB1), suggesting that NPL3 expression affects chromosome stability—an unexpected result based on its function in RNA metabolism. We further showed that NPL3 expression sensitizes cells to a microtubule depolymerizing agent. In addition, we have used separation of function mutants to show many of the SDLs discovered when overexpressing NPL3 are due to its role in translation, not transcription. SFRS1 has a known role in translation. Finally, we found that NPL3 expression suppresses the slow growth of an sgo1Δ strain that is defective in spindle tension sensing, further underscoring a role in the spindle checkpoint. The human ortholog of SGO1 (SGOL2) is upregulated in the PTEN loss signature. Thus common genes and gene functions are identified in multiple SDL screens showing the inter-relatedness of the genes in the PTEN loss signature.

Using separation of function, we have found that the majority of the SDL interactions found when overexpressing NPL3 (including CPR1) are due to its role in translation, not transcription. NPL3's ortholog, SFRS1, also has a known role in translation. See Michlewski G, Sanford J R, Cáceres J F (April 2008). "The splicing factor SF2/ASF regulates translation initiation by enhancing phosphorylation of 4E-BP1". *Mol. Cell* 30 (2): 179-89. This may be interesting because this does not involve calcineurin, therefore cyclosporin derivatives that do not inhibit the immune response may be effective at treating cancers with SFRS1 overexpressed.

In certain aspects the invention provides methods to determine the yeast-defined synthetic genetic interactions for genes showing significant expression changes in PTEN-deficient breast tumors. We will perform experiments in order to understand the biology underlying the genetic interactions defined from the high-throughput screens. In addition, we will verify these interactions by RNAi in PTEN-deficient breast cancer cell lines.

In certain aspects the invention provides methods to determine whether compounds with known activity against specific gene targets treat cancers with the identified genetic makeup. In certain aspects the invention provides use of compounds with known activity against specific gene targets to treat cancers with the identified genetic makeup.

The yeast CPR1 gene was identified in two different synthetic dosage lethal (SDL) screens. Based on this result the human orthologue CYPA was identified as a target for pharmacological inhibition in cancer cells.

Cyclophilin Inhibitors

The contents of all references, including but not limited to the structures, describing cyclophilin inhibitors are specifically incorporated herein by reference.

Figure 4:
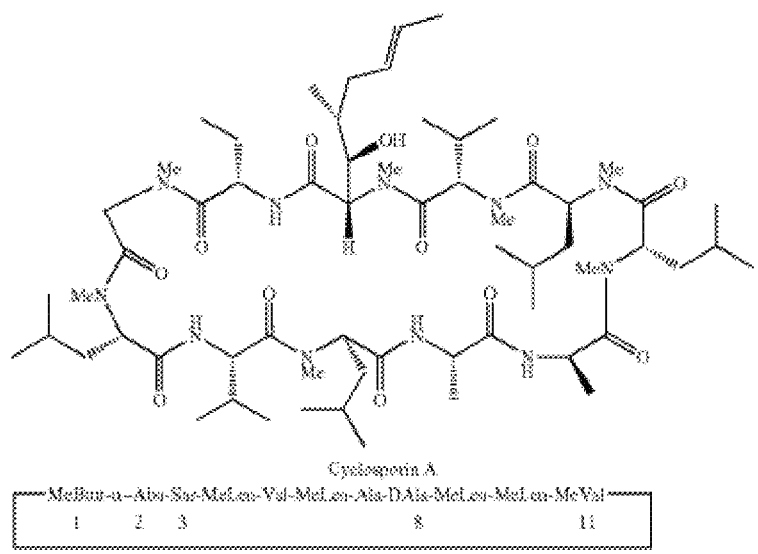
FIG. 4 shows the structure of cyclosporine A.

Cyclosporines, cyclosporine derivatives and analogues: The cyclosporins comprise a class of structurally distinctive, cyclic, poly-N-methylated undecapeptides, commonly possessing pharmacological, for example immunosuppressive, anti-inflammatory and/or antiparasitic activity. The first of the cyclosporins to be isolated was the naturally occurring fungal metabolite Ciclosporin or Cyclosporin, also known as cyclosporin A (FIG. 4).

Since the original discovery of Cyclosporin, a wide variety of naturally occurring cyclosporins have been isolated and identified, and many further non-natural cyclosporins have been prepared by total- or semi-synthetic means or by the application of modified culture techniques. The class comprised by the cyclosporins is thus now substantial and includes, for example, the naturally occurring cyclosporins A through Z [cf., Traber et al.; 1, Helv. Chim. Acta, 60, 1247-1255 (1977); Traber et al.; 2, Helv. Chim. Acta, 65, 1655-1667 (1982); Kobel et al.; Europ. J. Applied Microbiology and Biotechnology, 14, 273-240 (1982); and von Wartburg et al.; Progress in Allergy, 38, 28-45 (1986)], as well as various non-natural cyclosporin derivatives and artificial or synthetic cyclosporin derivatives and artificial or synthetic cyclosporins including dihydrocyclosporins [in which the -MeBmt-residue is saturated by hydrogenation]; derivatized cyclosporins (e.g., in which the 3'-O-atom of the -MeBmt-residue is acylated or a further substituent is introduced at the .alpha.-carbon atom of the sarcosyl residue at the 3-position); and cyclosporins in which variant amino acids are incorporated at specific positions within the peptide sequence, e.g. employing the total synthetic method for the production of cyclosporins developed by R. Wenger—see e.g. Traber et al., 1; Traber et al., 2; and Kobel et al., loc cit. U.S. Pat. Nos. 4,108,985, 4,220,641, 4,288,431, 4,554,351, 4,396,542 and 4,798,823; European Patent Publication Nos. 34,567A, 56,782A, 300,784A and 300,785; International Patent Publication No. WO 86/02080 and UK Patent Publication Nos. 2,206,119 and 2,207,678; Wenger 1, Transpl. Proc., 15 Suppl. 1:2230 (1983); Wenger 2, Angew. Chem. Int. Ed. 24 77 (1985) and Wenger 3, Progress in the Chemistry of Organic Natural Products, 50, 123 (1986).

Several synthetic modifications of the -MeBmt-residue residing at position 1 of the cyclosporin undecapeptide have been described including: Park et al., Tetrahedron Lett. 1989, 30, 4215-4218; U.S. Pat. Nos. 5,239,037, 5,293,057; U.S. Publication Nos. US20020142946, US20030087813, and US20030104992 assigned to Enanta Pharmaceuticals, Inc.; PCT Publication Nos. WO99/18120 and WO03/033526 both assigned to Isotechnika; and U.S. Pat. Nos. 4,384,996, 4,771,122, 5,284,826, and 5,525,590 assigned to Sandoz.

Other cyclosporine derivatives are also known. Eg. Kallen J, Mikol V, Taylor P, Walkinshaw M D. "X-ray structures and analysis of 11 cyclosporin derivatives complexed with cyclophilin A." J Mol Biol. Oct. 23, 1998; 283(2):435-49.

The compound cyclosporine (cyclosporine A or CsA) has found wide use since its introduction in the fields of organ transplantation and immunomodulation, and has brought about a significant increase in the success rate for transplantation procedures. Undesired side effects associated with cyclosporine, however, such as nephrotoxicity, have led to a continued search for immunosuppressant compounds having improved, efficacy and safety.

Side effects with systemic CsA include increase in diastolic blood pressure and decrease in renal function. Other side effects include hepatic dysfunction, hypertrichosis, tremor, gingival hyperplasis and paraesthsia. The systemic toxicity of CsA limits its use for the treatment of certain diseases. U.S. Pat. No. 7,468,419 provides cyclosporine derivatives with immunosuppressive activity.

Non-immunosuppressive cyclosporine derivatives: Cyclosporine derivatives which have reduced or lack immunosuppressive properties are also known. Described herein are non-limiting examples of non-immunosuppressive cyclosporine derivatives. See e.g., Victor L. Hsu, Ian M. Armitage "Solution structure of cyclosporin A and a nonimmunosuppressive analog bound to fully deuterated cyclophilin" Biochemistry, 1992, 31 (51), pp 12778-12784. Analogs of the immunosuppressive cyclic undecapeptide cyclosporin A (CsA) with substitutions in positions 1,4,6, and/or 11 were rationally designed to possess substantially diminished or no immunosuppressive activity. S R Bartz, E Hohenwalter, M K Hu, D H Rich, and M Malkovsky "Inhibition of human immunodeficiency virus replication by nonimmunosuppressive analogs of cyclosporin A." Proc Natl Acad Sci USA. Jun. 6, 1995; 92(12): 5381-5385.

Figure 5:
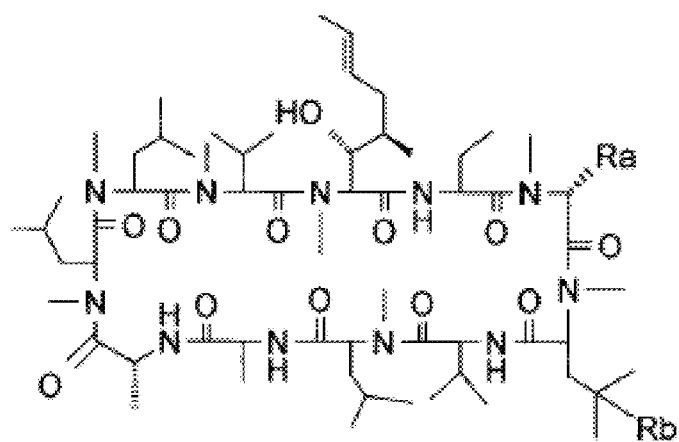
FIG. 5 shows the structure of cyclosporine A and two non-immunosuppressive cyclosporine derivatives: compound 211-810 (Formula I) and compound 209-825 (Formula II).
Figure 6A:
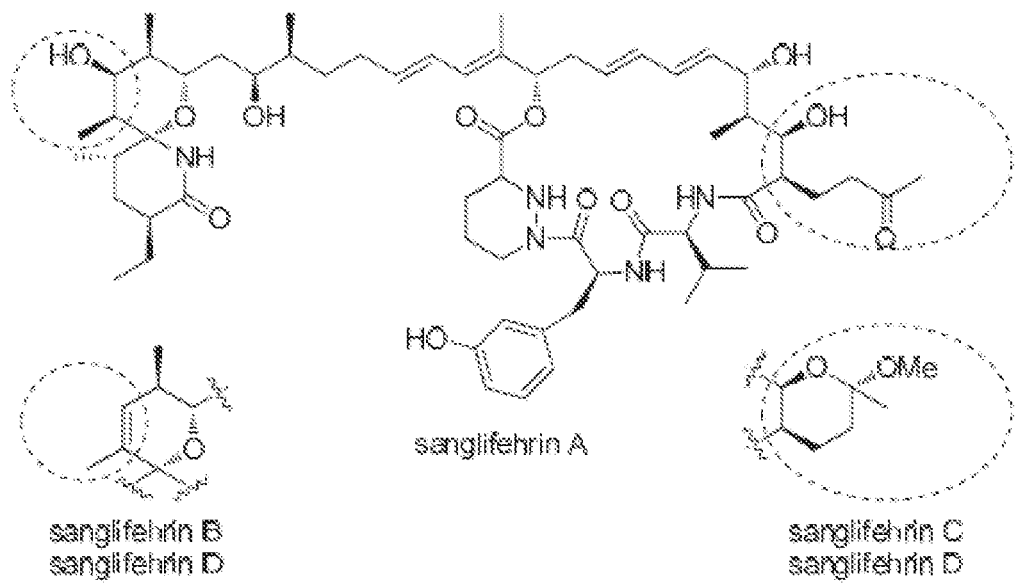
FIG. 6A shows structure of Sanglifehrins A-D.
Figure 6B:
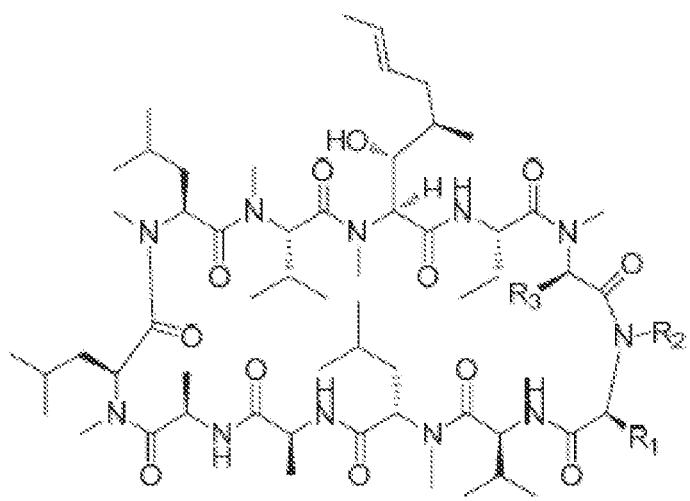
FIG. 6B shows structure of cyclosporines (CsA: R1=$CH_2CH(CH_3)_2$, R2=$CH_3$, R3=H, Alisporivir (DEBIO-025): R1=$CH(CH_3)_2$, R2=$CH_2CH_3$, R3=$CH_3$, SCY-635: R1=$CH_2C(CH_3)_2OH$, R2=$CH_3$, R3=$SCH_2N(CH_3)_2$, NIM-811: R1=$CH(CH_3)$ $CH_2CH_3$, R2=$CH_3$, R3=H) (Gregory M A, Bobardt M, Obeid S, Chatterji U, Coates N J, Foster T, Gallay P, Leyssen P, Moss S J, Neyts J, Nur-E-Alam M, Paeshuyse J, Piraee M, Suthar D, Warneck T, Zhang M Q, Wilkinson B. "Preclinical characterisation of naturally occurring polyketide cyclophilin inhibitors from the sanglifehrin family. *Antimicrob Agents Chemother.*" Mar. 7, 2011. [Epub ahead of print].

FIG. 5 shows examples of non-immunosuppressive cyclosporine derivatives. Adapted from Cruz M C, Del Poeta M, Wang P, Wenger R, Zenke G, Quesniaux V F, Movva N R, Perfect J R, Cardenas M E, Heitman J "Immunosuppressive and nonimmunosuppressive cyclosporine analogs are toxic to the opportunistic fungal pathogen Cryptococcus neoformans via cyclophilin-dependent inhibition of calcineurin." Antimicrob Agents Chemother. January 2000; 44(1):143-9.

A cyclosporine derivative, known as NIM811, is a non-immunosuppressive derivative. See e.g., Sue Ma, Joanna E. Boerner, ChoiLai TiongYip, Beat Weidmann, Neil S. Ryder, Michael P. Cooreman, and Kai Lin, "NIM811, a Cyclophilin Inhibitor, Exhibits Potent In Vitro Activity against Hepatitis C Virus Alone or in Combination with Alpha Interferon" Antimicrobial Agents and Chemotherapy, September 2006, p. 2976-2982, Vol. 50, No. 9; Motoyuki Kohjima, Munechika Enjoji, Nobito Higuchi, Kazuhiro Kotoh, Masaki Kato, Ryoiichi Takayanagi, and Makoto Nakamuta "NIM811, a nonimmunosuppressive cyclosporine analogue, suppresses collagen production and enhances collagenase activity in hepatic stellate cells" Liver Int. November 2007; 27(9): 1273-1281. Another non-immunosuppressive derivative is SCY-635. Sam Hopkins, Bernard Scorneaux, Zhuhui Huang, Michael G. Murray, Stephen Wring, Craig Smitley, Richard Harris, Frank Erdmann, Gunter Fischer, and Yves Ribeill "SCY-635, a Novel Nonimmunosuppressive Analog of Cyclosporine That Exhibits Potent Inhibition of Hepatitis C Virus RNA Replication In Vitro" Antimicrob Agents Chemother. February 2010; 54(2): 660-672. Published online Nov. 23, 2009. SDZ PSC 833 is a non-immunosuppressive cyclosporine known as valspodar. Roland P. Keller1, Hans J. Altermatt2, Kees Nooter3, Guenter Poschmann1, Jean A. Laissue2, Pietro Bollinger1, Peter C. Hiestand1, "SDZ PSC 833, A non-immunosuppressive cyclosporine: Its potency in overcoming P-glycoprotein-mediated multidrug resistance of murine leukemia" *International Journal of Cancer*, Volume 50, Issue 4, pages 593-597, 20 Feb. 1992. Valspodar is a nonimmunosuppressive, nonnephrotoxic cyclosporine derivative, which is approximately two- to tenfold more potent than cyclosporin A. Fisher, Eur J Cancer, 1996; 32A: 1082-1088. The chemical structure of valspodar is Cyclo [[(2S,4R,6E)-4-methyl-2-(methylamino)-3-oxo-6-octenoyl]-L-valyl-N-methylglycyl-N-methyl-L-leucyl-L-valyl-N-methyl-L-leucyl-L-alanyl-D-alanyl-N-methyl-L-leucyl-N-methyl- L-leucyl-N-methyl-L-valyl] (SEQ ID NO: 1) (CAS Registry Number 121584-18-7).

DEBIO-025 is another non-immunosuppressive derivative of cyclosporine. See Paeshuyse J, Kaul A, De Clercq E, Rosenwirth B, Dumont J M, Scalfaro P, Bartenschlager R, Neyts J. "The non-immunosuppressive cyclosporin DEBIO-025 is a potent inhibitor of hepatitis C virus replication in vitro. Hepatology." April 2006; 43(4):761-70.

Derivatives of cyclosporine are also described in WO2010/052559, the content of which publication is herein incorporated by reference in its entirety.

Non-limiting examples of non-immunosuppressive cyclosporine derivatives are listed in Table 2.

Table 2 shows cyclosporine derivatives of the structure Cyclo-($AXX_1$-$AXX_2$-$AXX_3$-$AXX_4$-$AXX_5$-$AXX_6$-$AXX_7$-$AXX_8$-$AXX_9$-$AXX_{10}$-$AXX_{11}$) (Formula IX) (SEQ ID NO: 2), where:

| | $AXX_1$ | $AXX_2$ | $AXX_3$ | $AXX_4$ | $AXX_5$ | $AXX_6$ | $AXX_7$ | $AXX_8$ | $AXX_9$ | $AXX_{10}$ | $AXX_{11}$ |
|---|---|---|---|---|---|---|---|---|---|---|---|
| CsA* | MeBmt | Abu | Sar | MeLeu | Val | MeLeu | Ala | D-Ala | MeLeu | MeLeu | MeVal |
| 8T2 | MeBmt | Thr | Sar | MeLeu | Leu | MeLeu | Ala | D-Hiv | MeLeu | Leu | MeVal |
| RLY-001 | MeBmt | Abu | D-MeAla | EtVal | Leu | MeLeu | Ala | D-Hiv | MeLeu | Leu | MeVal |
| RLY-018 | MeBmt | Val | D-MeAla | MeVal | Leu | MeLeu | Ala | D-Hiv | MeLeu | Leu | MeVal |
| RLY-045 | MeBmt | Abu | D-MeAla | MeVal | Val | MeAla | Ala | D-Hiv | MeLeu | Leu | MeVal |

-continued

| | AXX₁ | AXX₂ | AXX₃ | AXX₄ | AXX₅ | AXX₆ | AXX₇ | AXX₈ | AXX₉ | AXX₁₀ | AXX₁₁ |
|---|---|---|---|---|---|---|---|---|---|---|---|
| RLY-062 | MeBmt | Val | D-MeAla | MeVal | Leu | MeLeu | Gly | D-Hiv | MeLeu | Leu | MeVal |
| RLY-070 | MeBmt | Val | D-MeAla | MeVal | Val | Sar | Gly | D-Hiv | MeLeu | Leu | MeVal |

*CsA is included as a reference.

Formula III is 8T2. Formula IV is RLY-001. Formula V is RLY-018. Formula VI is RLY-045. Formula VII is RLY-062. Formula VIII is RLY-070.

The cyclosporines of Table 2 are described using the following naming nomenclature (See WO2010/052559). The cyclosporines of Table 2 comprise eleven residues, ten being α-amino acids and one being α-hydroxy acid. This α-hydroxy acid is (2R)-2-hydroxy-3-methyl-butanoic acid, also known as O-α-hydroxyisovaleric acid and abbreviated as H—O-Hiv-OH. In Formula (IX), this hydroxyl acid is in position 8. It forms on the carboxylic acid end an amide bond with the amino group of the α-amino acid in position 9, namely N-methyl-leucine, and, on the hydroxyl end an ester bond with the carboxylic acid group of the a-amino acid in position 7, namely alanine or glycine.

The α-amino acids of Formula (IX) are described using the three letter code abbreviation usually used to name amino acids and their configuration is L-configuration, unless otherwise specified. The residue numbering starts from AXX₁ representing N-methyl-(4R)-4-[(E)-2-butenyl]-4-methyl-L-threonine or MeBmt, or its structural derivatives. When an alkyl group such as a methyl group Me or an ethyl group Et appears before the abbreviation of an amino acid, this means that such an alkyl group is fixed on the amino group of said amino acid residue.

In certain aspects, the invention provides use of a pro-drug, an ester, or a pharmaceutically acceptable salt of any of the cyclosporines, cyclosporine derivatives and analogues used in the methods of the invention.

Sanglifehrins: Sanglifehrins are naturally occurring polyketide cyclophilin inhibitors. See Gregory M A, Bobardt M, Obeid S, Chatterji U, Coates N J, Foster T, Gallay P, Leyssen P, Moss S J, Neyts J, Nur-E-Alam M, Paeshuyse J, Piraee M, Suthar D, Warneck T, Zhang M Q, Wilkinson B. "Preclinical characterisation of naturally occurring polyketide cyclophilin inhibitors from the sanglifehrin family. *Antimicrob Agents Chemother.*" Mar. 7, 2011. [Epub ahead of print].

PARP Inhibitors

A non-limiting example of a PARP inhibitor used in the methods of the invention is olaparib.

DNA Cross-Linking Agents

Non-limiting examples of DNA cross-linking agents are mitomycin C, cyclophosphamide, chlorambucil, uramustine, ifosfamide, melphalan, bendamustine, carmustine, or any combination thereof.

The exact therapeutic amount will be determined by the practitioner, in light of factors related to the subject that requires treatment, and/or a disease or disorder which is treated. Therapeutic amount can be determined in dose escalation studies. Amount and administration are adjusted to provide sufficient levels of the active ingredient or to maintain the desired effect. Factors that may be taken into account include the severity of the disease or disorder, location of the affected tissue or cells within the body, general health of the subject, age, weight, and gender of the subject, diet, time and frequency of administration, drug combination(s), reaction sensitivities, and tolerance/response to therapy. Skilled artisans can readily determine the therapeutic amount which is necessary to treat a disease or a disorder, or the therapeutic amount which is necessary to prevent a disease or a disorder.

Normal dosage amounts may vary from 0.1 to 100,000 micrograms, up to a total dose of about 1 g, depending upon the route of administration. A non-limiting example of dosage may be in the range of 2.5 to 15 mg/kg. Guidance as to particular dosages and methods of delivery is provided in the literature and generally available to practitioners in the art. Those skilled in the art will employ formulations suitable for delivery of the therapeutic agents of the invention. The methods of the invention employ any suitable route of administration of the therapeutic agents.

Any suitable method of delivery may be used to administer the agents in the methods of the invention. The agents may be formulated in any suitable formulation for delivery and treatment of cancer.

Example 1

The invention provides methods to identify cancer-specific synthetic genetic interactions rapidly and inexpensively using the *Saccharomyces* model system, and then use these findings as a guide to develop and evaluate compounds, which are known to act against these targets, for cancer therapy, including, but not limited to, breast cancer therapy.

Disclosed herein are experiments to show feasibility of the approach of using yeast screens to identify human target genes. We performed a biological characterization of SDL interactions already identified in our screens. We then used the yeast-derived information to perform RNAi experiments to demonstrate that these interactions can affect breast cancer cells.

Example 1A

Provided herein are methods and experiments to define the biological mechanisms of the SDL interactions from yeast. In one step, we verified the SDL interactions identified in high throughput screens with individual experiments by rescreening the affected genes from the high throughput studies followed by experiments on individual strains to ensure that the effects are 'on target' and not spurious mutations. As an example of the biological characterizations we performed, we showed how NPL3 gene expression impinges on the DNA damage and mitotic checkpoints. An analysis of various damaging agents during NPL3 expression were made to determine if NPL3 expression sensitizes these strains to damage. We also assayed molecular indicators of checkpoint function in wild-type cells and cells over-expressing NPL3. We also monitored checkpoints after inducing damage to determine whether NPL3 expression is suppressing checkpoint activation. These experiments provided an overview of the major checkpoint functions during the cell cycle and allowed us to focus on the S or G2/M checkpoints.

Example 1B

Human orthologs of genes that have been defined in the yeast SDL screens were used to screen the breast tumor cell lines from which the query genes were identified. We concentrated on NPL3/SFRS1 as the founding example. Based on the PTEN-expression profile, SFRS1 is over-expressed in PTEN negative cancer. SFRS1 is also overexpressed in certain PTEN+ tumors, for example but not limited to ovarian neoplasias. One gene that showed an SDL interaction with NPL3 over-expression was CPR1. The human orthologue of NPL3 is SFRS1 and the human orthologue of CPR1 is CPYA. Protein levels in mammalian cells can be monitored by immunohistochemistry (Ab available from Abcam). Lentiviral shRNA vectors (pGIPZ, Open Biosystems) will be obtained for the interacting SDL partner genes. We will evaluate the SDL in 5 PTEN+ and 5 PTEN− breast tumor lines by transducing them with the lentiviral shRNA vectors and comparing the effects on growth after transduction with a control GFP reporter vector. In each case, the lentiviral-encoded shRNAs are appended to the GFP reporter transcript so that shRNA processing and expression down-regulation can be correlated with levels of GFP expression (i.e., more viral integrations=more GFP=more shRNA). Thus, the effect of gene knockdown in a tumor cell line will be evaluated by comparing the GFP expression profiles of the shRNA vector and a control GFP vector by FACS. A positive result is indicated when the SDL partners of SFRS1 show decreased viability when down-regulated in the PTEN− tumors but are unaffected in the PTEN+ tumor lines. Total RNA and protein extracts will be recovered from transduced cell lines to evaluate the extent of down-regulation. Both quantitative PCR and protein blots, depending on antibody availability, will be used to measure the effects of the shRNA experiment. We also evaluate the level of SFRS1 expression in all of the cell lines and determine whether SDL correlates with SFRS1 expression levels as anticipated.

Example 2

Compounds with known activity against specific gene targets were queried for their affect against cancers with the identified genetic makeup. One such class of compounds is cyclosporine and its derivative and analogues which target cyclophilins. Some of these compounds inhibit metabolic processes and vary in their level of preclinical development. Each of these compounds will be tested against the set of PTEN null and PTEN wild type breast cancer cell lines using dose response cytotoxicity assays and colony formation assays. In addition, we will employ a set of isogenic cell lines with each variation of PTEN loss, EGFR overexpression, and dominant negative p53 overexpression (triple modified) which mimics the typical PTEN null basal-like breast cancer that heavily influenced the PTEN signature. These cell lines will be used as an adjunct to dissect the role of these alterations in identified synthetic lethal interactions.

The set of genes identified in the screens so far show significant enrichment for two cell processes, namely maintenance of chromosomal stability and fatty acid metabolism. We will therefore test the synthetic lethality of inhibiting key proteins involved in these processes and pathways. PARP inhibition and the DNA cross-linking agent cisplatin have already shown SL interactions with PTEN loss and they target chromosomal stability[33].

In certain aspects the invention provides methods to treat cancer, including but not limited to PTEN-deficient cancer, using a combination of agents targeting chromosomal stability pathways and metabolic pathways simultaneously using the compounds identified above in combination with either PARP inhibition or cisplatin. Given that fatty acids stimulate AMPK activity it is likely that tumors have evolved a mechanism to overcome this negative feedback, thus opening up a therapeutic opportunity to turn AMPK back on with its known activators metformin or pemetrexed[34], both of which are FDA approved drugs. Therefore, the trifecta of AMPK activation, inhibition of fatty acid synthesis, and induced chromosomal damage may be a potent cocktail against PTEN null cells and underscores the power of understanding the critical pathways subverted by specific tumors with specific lesions. Identified SL compounds in vitro will be confirmed in vivo in a xenograft experiment.

In certain aspects, the invention provides methods of identifying, validating, and translating targets of SL interactions with PTEN loss. Finding novel targets and drugs that can kill PTEN null cancer cells cannot be understated given that PTEN null tumors are highly lethal with few known effective therapies; examples including triple negative breast cancers (i.e., do not express significant amounts of estrogen receptor, progesterone receptor, or HER2) and hormone resistant prostate cancers (i.e., prostate cancers which grow in the setting of low testosterone levels).

Example 3

PTEN Deficiency Sensitizes Cancer Cells to Cyclosporin A

Upon observing a synthetic lethal interaction between loss of the gene CPR1 in a simulated PTEN null background (NPL3 overexpression) in *Saccharomyces cerevisiae*, we aimed to examine if this interaction carried over to mammalian system, specifically in PTEN null cancer cells. The yeast gene Cpr1 is homologous to the human gene CYPA, cytoplasmic peptdyl-prolyl cis-trans isomerase, or cyclophilin A. Given that the drug cyclosporin A (ciclosporin, cyclosporine, CsA) can bind to cyclophilin we tested the sensitivity of multiple isogenic cancer cell lines, with and without PTEN, to CsA. Our in vitro experiments revealed that PTEN deficiency sensitizes cancer cells to CsA.

Figure 1:
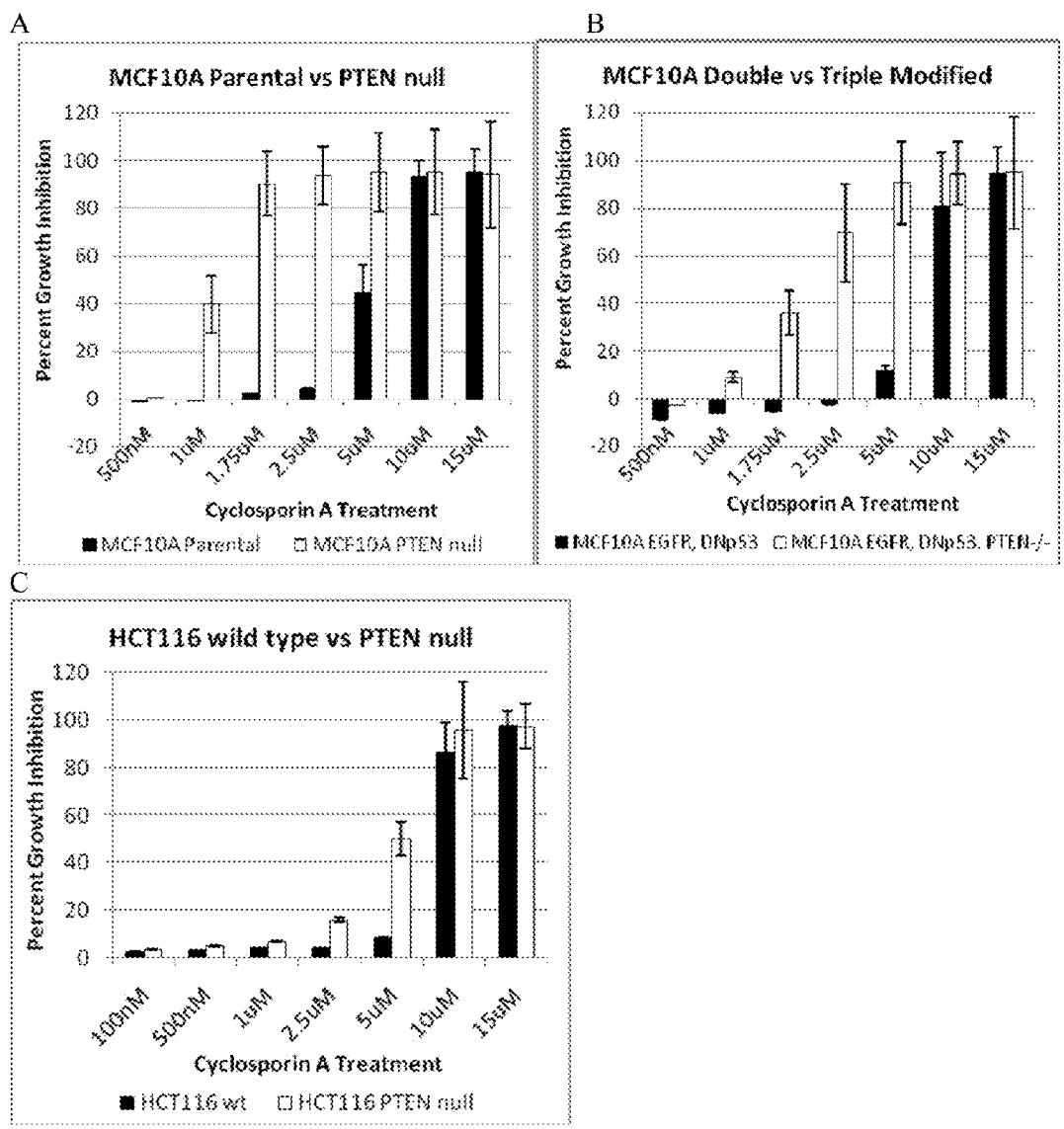
FIG. 1 shows growth inhibition effects of cyclosporin A.

When exposed to CsA, MCF10A parental mammary epithelial cells with wild type PTEN demonstrated an IC50 of up to five times greater than its MCF10A PTEN null counterpart (IC50 of 5 uM compared to 1.08 uM respectively). In the range from 1 uM to 2.5 uM, the MCF10A PTEN null line was more sensitive (about 20-30 fold) to CsA than the parental line. In this range, the PTEN null line experienced a dose effect on growth inhibition while the parental remained insensitive to the drug and continued to proliferate. At 1.75 uM, a greater than 30 fold difference in growth inhibition was observed between these two lines. (FIG. 1A).

This large difference in proliferation inhibition is seen across a broader range of doses in another MCF10A isogenic set that has EGFR overexpression and dominant-negative p53. The PTEN null version of this line, identified as MCF10A triple modified, had an IC50 of 2 uM compared to the MCF10A double modified line with wild type PTEN IC50 of 7.1 uM. Again, the more significant effect of CsA is observed by looking at the percent growth inhibition between 1 uM to 5 uM, where the double modified line is insensitive to the drug, but the PTEN null triple modified line is up to sixty times more sensitive. (FIG. 1B)

We also tested this effect in a colon cancer isogenic set, HCT116 wild type versus PTEN null. The general trend of PTEN null conferring greater sensitivity to CsA was observed, but to a less dramatic effect. The IC50 difference between the HCT116 PTEN null and wild type lines was less than 2 fold; the largest difference in growth inhibition was observed at 5 uM, yet was still less than a six fold difference. We hypothesize that the known and potent genetic alterations already present in this isogenic line, including a KRAS mutation and a PIK3CA mutation, maintains baseline PI3K pathway activation and thus would significantly dampen any synthetic lethal interaction. (FIG. 1C).

We have tested the sensitivity to CsA in a larger set of breast cancer cell lines. In general, we observe that breast cancer cells that are PTEN null have lower IC50s, all below 8 uM, compared to breast cancer cells with wild type PTEN. Most wild type lines have an IC50 of greater than 15 uM. The PTEN wild type cell line MDA-MB-231 is an outlier, having a very low IC50 of 1.9 uM; this line is also a KRAS mutant, interferon in recurrent ovarian cancer: a California Cancer Consortium Trial." Int J Gynecol Cancer. March-April 2007; 17(2):373-8.

Mechanistic studies are ongoing and once mechanism is identified the possibility of optimization of the effect is likely significant.

Example 4

SFA (sanglifehrin A) and NIM811 are tested for their effect on PTEN negative cancer cells in, for example, but not limited to, experiments as described in Example 3.

Example 5

Table 3 shows experiments to elucidate sensitivity of PTEN negative cells to cyclophilin inhibitors

Figure 2:
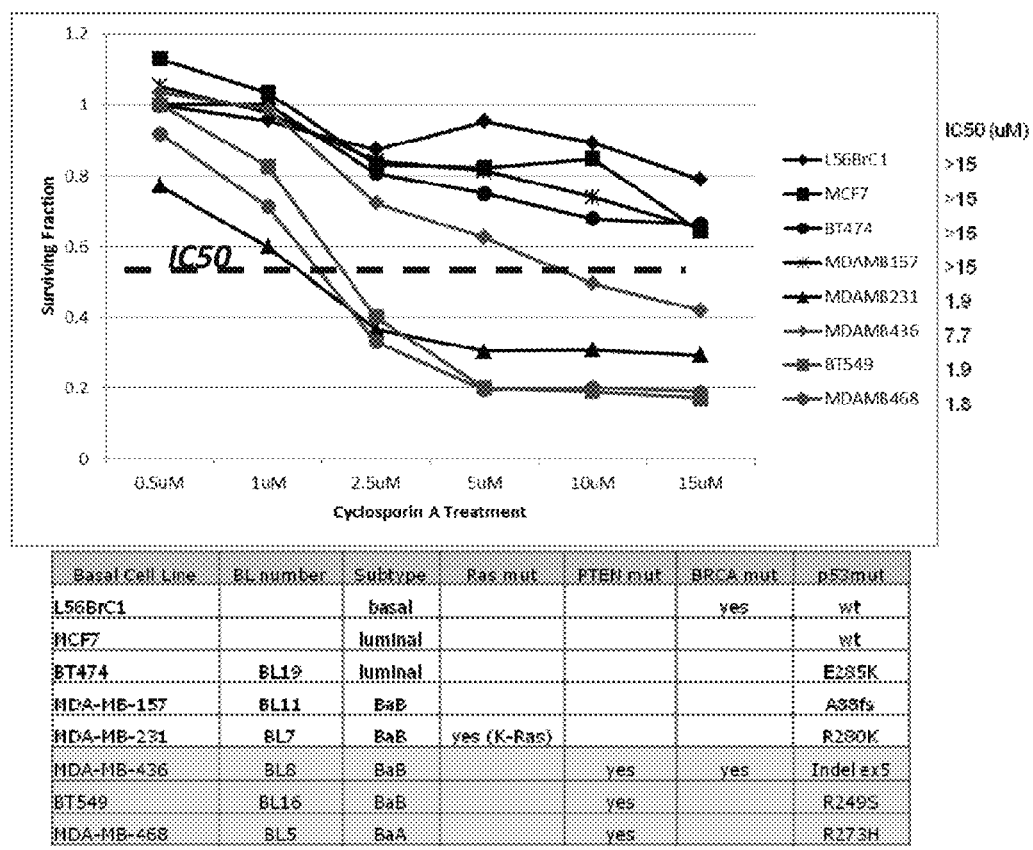
FIG. 2 shows cancer cell panel of survival to Cyclosporin A. Cell survival and proliferation of multiple cancer cell lines tested when exposed to cyclosporin A. Cells were plated in 48 well plates and treated with drug for ten days before quantifying cell proliferation using crystal violet assays.

| Experiment | Aim |
| --- | --- |
| Tacrolimus proliferation assay on +/− PTEN isogenic pairs | CsA working via calcineurin pathway/inhibiting NFAT? |
| CsA proliferation assay on MCF10As with wt and mutant PTEN (G129E & C124S) transfected back in (rescue assay) | Show PTEN loss is making cells sensitive to CsA by rescuing them with PTEN Determine if catalytic part of PTEN diminished sensitivity to CsA |
| Show apoptosis at 2.5 and 5uM CsA in 2 sensitive and 2 resistant (PTEN wt) cell lines | |
| NIM811 CsA analog proliferation assay | Confirm mechanism not via calcineurin pathway (mitochondrial permeability transition inhibitor?) |
| Test PPIase activity +/− CsA is isogenic sets | Is CsA functioning by altering PPIase activity of cyclophilin A preferentially in PTEN−/− cells? |
| SFA (sanglifehrin A) proliferation assay | Mechanism via CypA alone vs calcineruin pathway |
| CypA WB with CsA treatment for levels of CypA | Mechanism via regulation of CypA? |
| Proliferation assays in hypoxic conditions | Mechanism via hypoxia? |
| Test CsA + Cisplatin (other DNA cross-linking agents) synergy in isogenic pairs: 1) proliferation assay on +/− PTEN isogenic pairs 2) Cleaved caspase 3 WB 3) pAKT WB | Test for synergy Enhanced apoptosis? PI3K pathway activated? |
| PI3K WB of CsA treatment in isogenic sets | Is PI3K pathway activated preferentially upon CsA treatment? |
| ROS detection | ROS generation mechanism for CsA sensitivity in PTEN null cells? | supporting a hypothesis that such a mutation could alter the synthetic lethal interaction. (FIG. 2).

Figure 3:
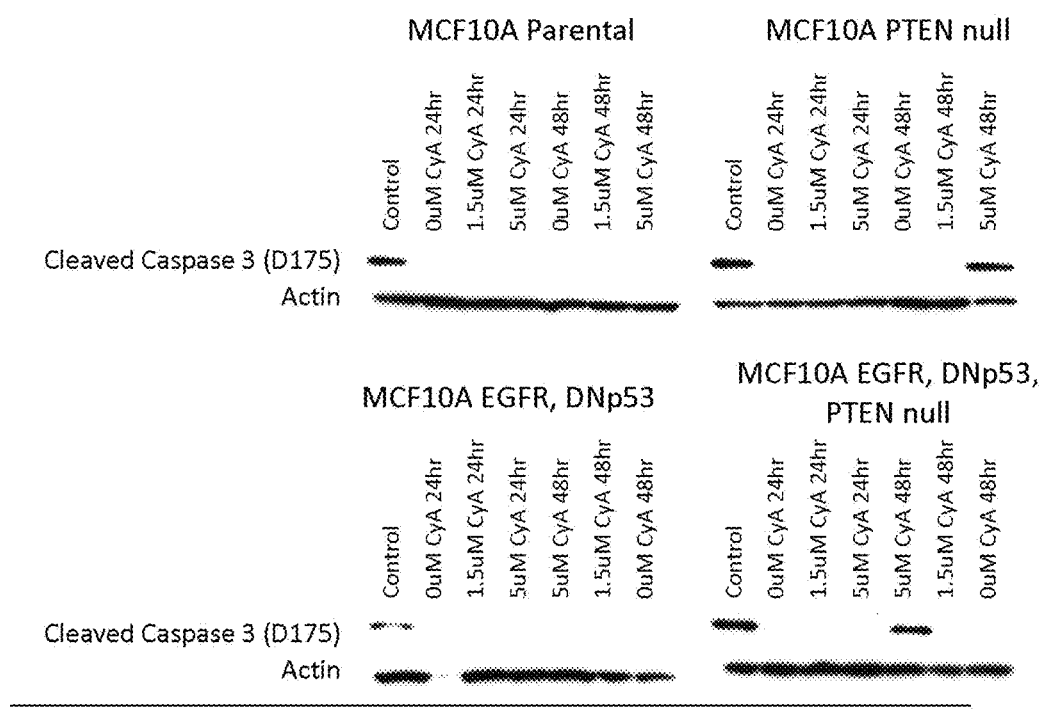
FIG. 3 shows that PTEN null cells undergo apoptosis upon exposure to cyclosporin A. Cleaved caspase 3 western blotting indicates PTEN null cells are undergoing apoptosis when exposed to 5 uM cyclosporin A for 48 hours, while parental cells do not. The control used is breast cancer cell line MDAMB468 treated with 800 nM doxorubicin for 48 hours.

The same two MCF10A isogenic lines demonstrate that the PTEN null cells are undergoing robust apoptosis with exposure to CsA, but parental lines are not at the same dose and length of treatment. This was measured by observing levels of cleaved caspase 3 at 24 and 48 hours of exposure to 0, 1.5 or 5 uM CsA. (FIG. 3).

Infusional CsA has been in used in multiple cancer clinical trials with the goal of overcoming resistance to chemotherapy through inhibition of efflux pumps. A few of these trials have demonstrated that in vivo drug levels of 2.5 uM are achievable. See Chambers S K, Davis C A, Chambers J T, Schwartz P E, Lorber M I, Hschumacher R E. "Phase I trial of intravenous carboplatin and cyclosporin A in refractory gynecologic cancer patients." *Clin Cancer Res*. October 1996; 2(10):1699-704; Morgan R J Jr, Synold T W, Gandara D, Muggia F, Scudder S, Reed E, Margolin K, Raschko J, Leong L, Shibata S, Tetef M, Vasilev S, McGonigle K, Longmate J, Yen Y, Chow W, Somlo G, Carroll M, Doroshow J H. "Phase II trial of carboplatin and infusional cyclosporine with alpha-

Example 6

Non-Immunosuppressive Cyclosporines Affect Growth of Cancer Cells

Non-immunosuppressive cyclosporines of Formula III (8T2), Formula IV (RLY-001), Formula V (RLY-018), Formula VI (RLY-045), Formula VII (RLY-062), and Formula VIII (RLY-070) were tested for their effect on PTEN negative cancer cells (FIG. 9). MCF10A wild type (WT) and PTEN knockout (PT−/−) cells were seeded into 48-well plate with density of 4000 cells/well. The next day, the growth medium was changed to medium containing a compound, CsA or its analogs of Formula III-VIII. Medium containing 0.1% DMSO, was used as a negative control. Ninety six (96) hours after treatment, the cells were stained with crystal violet for cell growth. The cell growth of negative control group was set as 100%.

These data demonstrated that a non-immunosuppressive CsA analog has the same inhibitory effect on PTEN null cells as CsA. Any other PTEN negative cancer cell line can be used.

Figure 8:
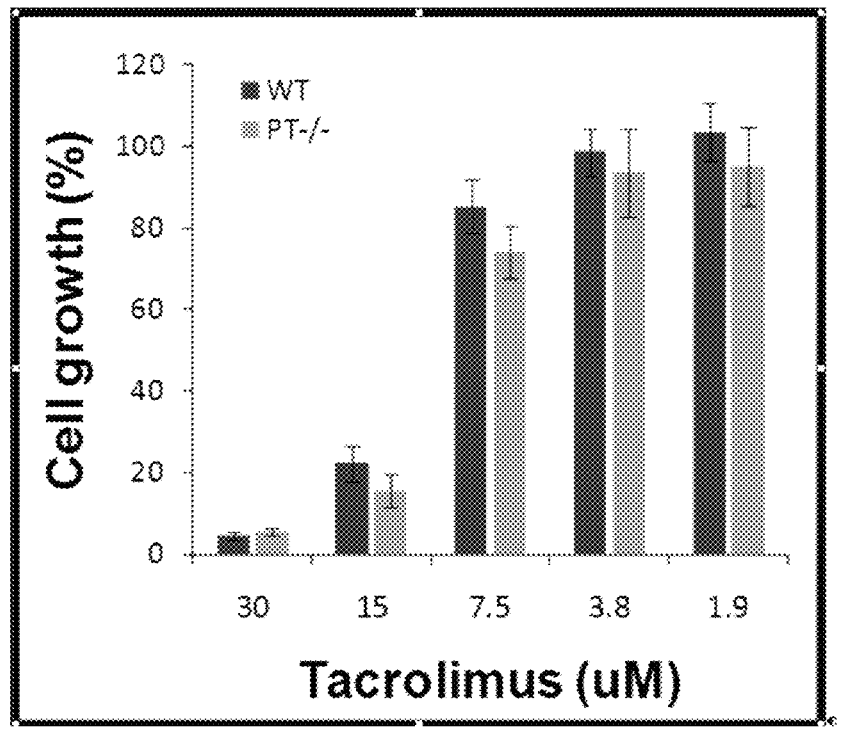
FIG. 8 shows cell growth inhibition by Tacrolimus on MCF10A cells. MCF10A wild type (WT) and PTEN knockout (PT−/−) cells were seeded into 48-well plate with density of 4000 cells/well. The next day, the growth medium was changed to a medium containing Tacrolimus. Medium containing 0.1% DMSO was used as negative control. Ninety-six
Figure 9A:
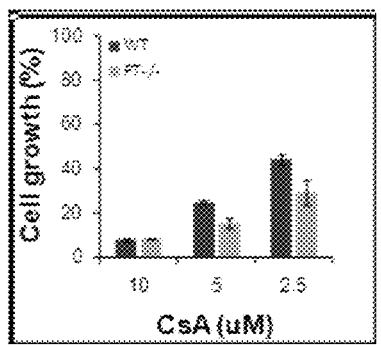
Figure 9B:
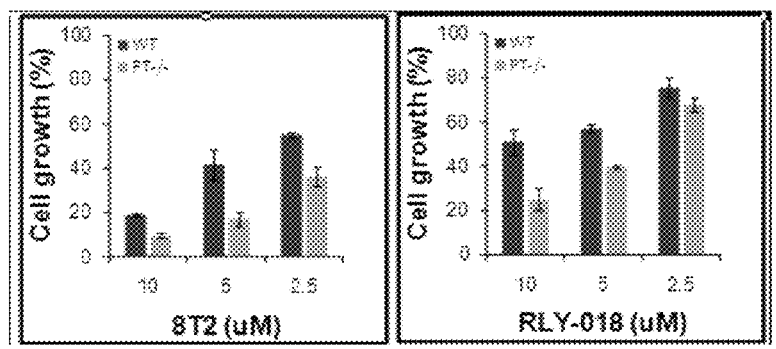
Figure 9C:
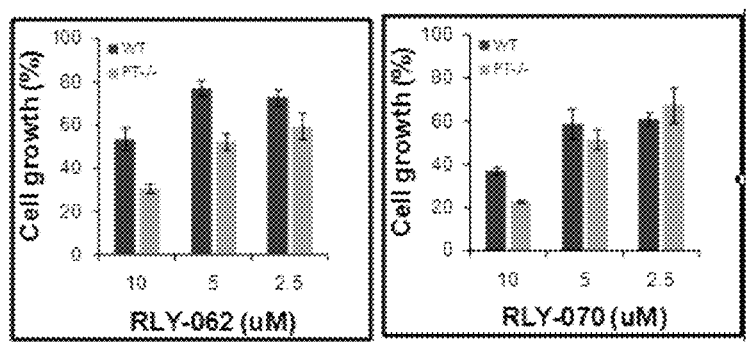
Figure 9D:
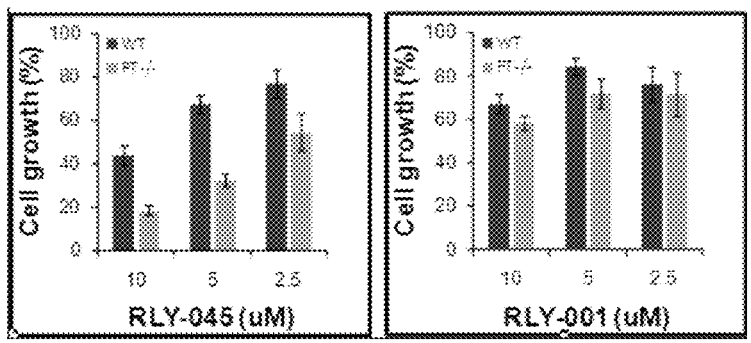

This idea is bolstered by data (FIG. 8) showing that tacrolimus, another immunosuppressant whose mechanism of immunosuppression is like CsA, is mediated by calcineurin inhibition, does not inhibit cancer cells at physiologic dosing and does not preferentially kill PTEN null cells.

The non-immunosuppressive Cyclosporine analog, NIM-811, was tested for its effect on PTEN negative cancer cells (FIGS. 10A and 10B). MCF10A wild type (WT) and PTEN knockout (PT−/−) cells were seeded into 48-well plates at a density of 4000 cells/well. The next day, the growth medium was changed to medium containing Cyclosporine A (CsA) and the non-immunosuppressive Cyclosporine analog, NIM-811. Medium containing 0.1% DMSO was used as negative control. Ninety-six (96) hours after treatment, the cells were stained with crystal violet and measured for cell growth. Cell growth of the negative control group was set as 100% (FIG. 10A).

MDA-MB-468 cells (PT−/−) were seeded into 48-well plates at a density of 5000 cells/well. The next day, the growth medium was changed to medium containing CsA and NIM-811. Medium containing 0.1% DMSO was used as negative control. The medium was replenished once. Seven days after treatment, the cells were stained with crystal violet and measured for cell growth. Cell growth of the negative control group is set as 100% (FIG. 10B).

NIM-811 shows increased activity compared to CsA to differentially inhibit PT−/− MCF10A cells vs. isogenic wild type (WT) cells. On the PT−/− breast cancer cell line, MDA-MB-468, NIM-811 shows better cell growth inhibition activity compared to CsA. These results further support the notion that PTEN−/− cancer cells are more sensitive to Cyclosporine analogues than their wild type counterparts.

REFERENCES

1. *Cancer Facts and Figures* 2010. Atlanta: American Cancer Society; 2010 2010.
2. Kraus M H, Popescu N C, Amsbaugh S C, King C R. Overexpression of the EGF receptor-related proto-oncogene erbB-2 in human mammary tumor cell lines by different molecular mechanisms. *Embo J*. March 1987; 6(3): 605-610.
3. Slamon D J, Clark G M, Wong S G, Levin W J, Ullrich A, McGuire W L. Human breast cancer: correlation of relapse and survival with amplification of the HER-2/neu oncogene. *Science*. Jan. 9 1987; 235(4785):177-182.
4. Bryant H E, Schultz N, Thomas H D, Parker K M, Flower D, Lopez E, Kyle S, Meuth M, Curtin N J, Helleday T. Specific killing of BRCA2-deficient tumours with inhibitors of poly(ADP-ribose) polymerase. *Nature*. Apr. 14 2005; 434(7035):913-917.
5. Farmer H, McCabe N, Lord C J, Tutt A N, Johnson D A, Richardson T B, Santarosa M, Dillon K J, Hickson I, Knights C, Martin N M, Jackson S P, Smith G C, Ashworth A. Targeting the DNA repair defect in BRCA mutant cells as a therapeutic strategy. *Nature*. Apr. 14 2005; 434(7035): 917-921.
6. Saal L H, Johansson P, Holm K, Gruvberger-Saal S K, She Q B, Maurer M, Koujak S, Ferrando A A, Malmstrom P, Memeo L, Isola J, Bendahl P O, Rosen N, Hibshoosh H, Ringner M, Borg A, Parsons R. Poor prognosis in carcinoma is associated with a gene expression signature of aberrant PTEN tumor suppressor pathway activity. *Proc Natl Acad Sci USA*. May 1 2007; 104(18):7564-7569.
7. Wong K K, Engelman J A, Cantley L C. Targeting the PI3K signaling pathway in cancer. *Curr Opin Genet Dev*. Dec. 11 2009.
8. Salmena L, Carracedo A, Pandolfi P P. Tenets of PTEN tumor suppression. *Cell*. May 2 2008; 133(3):403-414.
9. Podsypanina K, Lee R T, Politis C, Hennessy I, Crane A, Puc J, Neshat M, Wang H, Yang L, Gibbons J, Frost P, Dreisbach V, Blenis J, Gaciong Z, Fisher P, Sawyers C, Hedrick-Ellenson L, Parsons R. An inhibitor of mTOR reduces neoplasia and normalizes p70/56 kinase activity in Pten+/− mice. *Proc Natl Acad Sci USA*. Aug. 28 2001; 98(18):10320-10325.
10. Cantley L C. The phosphoinositide 3-kinase pathway. *Science*. May 31 2002; 296(5573):1655-1657.
11. Engelman J A, Luo J, Cantley L C. The evolution of phosphatidylinositol 3-kinases as regulators of growth and metabolism. *Nat Rev Genet*. August 2006; 7(8):606-619.
12. Samuels Y, Ericson K. Oncogenic PI3K and its role in cancer. *Curr Opin Oncol*. January 2006; 18(1):77-82.
13. Saal L H, Holm K, Maurer M, Memeo L, Su T, Wang X, Yu J S, Malmstrom P O, Mansukhani M, Enoksson J, Hibshoosh H, Borg A, Parsons R. PIK3CA mutations correlate with hormone receptors, node metastasis, and ERBB2, and are mutually exclusive with PTEN loss in human breast carcinoma. *Cancer Res*. Apr. 1 2005; 65(7): 2554-2559.
14. Kroll E S, Hyland K M, Hieter P, Li J J. Establishing genetic interactions by a synthetic dosage lethality phenotype. *Genetics*. May 1996; 143(1):95-102.
15. Measday V, Hailey D W, Pot I, Givan S A, Hyland K M, Cagney G, Fields S, Davis T N, Hieter P. Ctf3p, the Mis6 budding yeast homolog, interacts with Mcm22p and Mcm16p at the yeast outer kinetochore. *Genes Dev*. Jan. 1 2002; 16(1):101-113.
16. Measday V, Hieter P. Synthetic dosage lethality. *Methods Enzymol*. 2002; 350:316-326.
17. Khurana V, Lindquist S. Modelling neurodegeneration in *Saccharomyces cerevisiae*: why cook with baker's yeast? *Nat Rev Neurosci*. June; 11(6):436-449.
18. Heinicke S, Livstone M S, Lu C, Oughtred R, Kang F, Angiuoli S V, White O, Botstein D, Dolinski K. The Princeton Protein Orthology Database (P-POD): a comparative genomics analysis tool for biologists. *PLoS One*. 2007; 2(1):e766.
19. Giorgini F, Guidetti P, Nguyen Q, Bennett S C, Muchowski P J. A genomic screen in yeast implicates kynurenine 3-monooxygenase as a therapeutic target for Huntington disease. *Nat Genet*. May 2005; 37(5):526-531.
20. Willingham S, Outeiro T F, DeVit M J, Lindquist S L, Muchowski P J. Yeast genes that enhance the toxicity of a mutant huntingtin fragment or alpha-synuclein. *Science*. Dec. 5 2003; 302(5651):1769-1772.
21. Bennett C B, Westmoreland T J, Verrier C S, Blanchette C A, Sabin T L, Phatnani H P, Mishina Y V, Huper G, Selim A L, Madison E R, Bailey D D, Falae A I, Galli A, Olson J A, Greenleaf A L, Marks J R. Yeast screens identify the RNA polymerase II CTD and SPT5 as relevant targets of BRCA1 interaction. *PLoS One*. 2008; 3(1):e1448.
22. Collins S R, Miller K M, Maas N L, Roguev A, Fillingham J, Chu C S, Schuldiner M, Gebbia M, Recht J, Shales M, Ding H, Xu H, Han J, Ingvarsdottir K, Cheng B, Andrews B, Boone C, Berger S L, Hieter P, Zhang Z, Brown G W, Ingles C J, Emili A, Allis C D, Toczyski D P, Weissman J S, Greenblatt J F, Krogan N J. Functional dissection of protein complexes involved in yeast chromosome biology using a genetic interaction map. *Nature*. Feb. 21 2007.
23. Costanzo M, Baryshnikova A, Bellay J, Kim Y, Spear E D, Sevier C S, Ding H, Koh J L, Toufighi K, Mostafavi S, Prinz J, St Onge R P, VanderSluis B, Makhnevych T, Vizeacoumar F J, Alizadeh S, Bahr S, Brost R L, Chen Y, Cokol M, Deshpande R, Li Z, Lin Z Y, Liang W, Marback M, Paw J, San Luis B J, Shuteriqi E, Tong A H, van Dyk N, Wallace I M, Whitney J A, Weirauch M T, Zhong G, Zhu H, Houry W A, Brudno M, Ragibizadeh S, Papp B, Pal C, Roth F P, Giaever G, Nislow C, Troyanskaya O G, Bussey H, Bader G D, Gingras A C, Morris Q D, Kim P M, Kaiser C A, Myers C L, Andrews B J, Boone C. The genetic landscape of a cell. *Science*. Jan. 22 2010; 327(5964):425-431.
24. Tong A H, Lesage G, Bader G D, Ding H, Xu H, Xin X, Young J, Berriz G F, Brost R L, Chang M, Chen Y, Cheng X, Chua G, Friesen H, Goldberg D S, Haynes J, Humphries C, He G, Hussein S, Ke L, Krogan N, Li Z, Levinson J N, Lu H, Menard P, Munyana C, Parsons A B, Ryan O, Tonikian R, Roberts T, Sdicu A M, Shapiro J, Sheikh B, Suter B, Wong S L, Zhang L V, Zhu H, Burd C G, Munro S, Sander C, Rine J, Greenblatt J, Peter M, Bretscher A, Bell G, Roth F P, Brown G W, Andrews B, Bussey H, Boone C. Global mapping of the yeast genetic interaction network. *Science*. Feb. 6 2004; 303(5659):808-813.
25. Liu X, Shi Y, Giranda V L, Luo Y Inhibition of the phosphatidylinositol 3-kinase/Akt pathway sensitizes MDA-MB468 human breast cancer cells to cerulenin-induced apoptosis. *Mol Cancer Ther*. March 2006; 5(3):494-501.
26. He Y, Liu J, Durrant D, Yang H S, Sweatman T, Lothstein L, Lee R M. N-benzyladriamycin-14-valerate (AD198) induces apoptosis through protein kinase C-delta-induced phosphorylation of phospholipid scramblase 3. *Cancer Res*. Nov. 1 2005; 65(21):10016-10023.
27. McGuire J J, Haile W H, Valiaeva N, Bartley D, Guo J, Coward J K. Potent inhibition of human folylpolyglutamate synthetase by a phosphinic acid mimic of the tetrahedral reaction intermediate. *Biochem Pharmacol*. Feb. 1 2003; 65(3):315-318.
28. Lopez-Ramos M, Prudent R, Moucadel V, Sautel C F, Barette C, Lafanechere L, Mouawad L, Grierson D, Schmidt F, Florent J C, Filippakopoulos P, Bullock A N, Knapp S, Reiser J B, Cochet C. New potent dual inhibitors of CK2 and Pim kinases: discovery and structural insights. *FASEB J*. May 3 2010.
29. Bachovchin D A, Brown S J, Rosen H, Cravatt B F. Identification of selective inhibitors of uncharacterized enzymes by high-throughput screening with fluorescent activity-based probes. *Nat Biotechnol*. April 2009; 27(4):387-394.
30. Piaggi S, Raggi C, Corti A, Pitzalis E, Mascherpa M C, Saviozzi M, Pompella A, Casini A F. Glutathione transferase omega 1-1 (GSTO1-1) plays an anti-apoptotic role in cell resistance to cisplatin toxicity. *Carcinogenesis*. May 2010; 31(5):804-811.
31. Dowling R J, Zakikhani M, Fantus I G, Pollak M, Sonenberg N. Metformin inhibits mammalian target of rapamycin-dependent translation initiation in breast cancer cells. *Cancer Res*. Nov. 15 2007; 67(22):10804-10812.
32. Zhou G, Myers R, Li Y, Chen Y, Shen X, Fenyk-Melody J, Wu M, Ventre J, Doebber T, Fujii N, Musi N, Hirshman M F, Goodyear L J, Moller D E. Role of AMP-activated protein kinase in mechanism of metformin action. *J Clin Invest*. October 2001; 108(8):1167-1174.
33. Mendes-Pereira A M, Martin S A, Brough R, McCarthy A, Taylor J R, Kim J S, Waldman T, Lord C J, Ashworth A. Synthetic lethal targeting of PTEN mutant cells with PARP inhibitors. *EMBO Mol Med*. September 2009; 1(6-7):315-322.
34. Racanelli A C, Rothbart S B, Heyer C L, Moran R G. Therapeutics by cytotoxic metabolite accumulation: pemetrexed causes ZMP accumulation, AMPK activation, and mammalian target of rapamycin inhibition. *Cancer Res*. Jul. 1 2009; 69(13):5467-5474.

What is claimed is:

1. A method to treat a phosphatase and tensin homolog (PTEN) negative cancer in a subject in need of treatment thereof, the method comprising contacting a PTEN negative cancer in the subject with a cyclosporine, wherein the cancer is breast cancer, prostate cancer, colon cancer, glioblastoma, endometrial cancer, lung cancer, thyroid cancer, lymphomas, ovarian cancer, or a combination thereof.

2. A method to reduce growth of a phosphatase and tensin homolog (PTEN) negative cancer cell in a subject in need of treatment thereof, the method comprising:
   contacting a PTEN negative cancer cell in the subject with a therapeutic amount of a cyclosporine, whereby the growth of the cancer is reduced compared to PTEN positive cancer cells, wherein the cancer is breast cancer, prostate cancer, colon cancer, glioblastoma, endometrial cancer, lung cancer, thyroid cancer, lymphomas, ovarian cancer, or a combination thereof.

3. A method to induce apoptosis of a phosphatase and tensin homolog (PTEN) negative cancer cell in a subject in need of treatment thereof, the method comprising:
   contacting a PTEN negative cancer cell in the subject with a therapeutic amount of a cyclosporine, whereby apoptosis of the cancer cell is induced and the subject is treated, wherein the cancer is breast cancer, prostate cancer, colon cancer, glioblastoma, endometrial cancer, lung cancer, thyroid cancer, lymphomas, ovarian cancer, or a combination thereof.

4. A method to treat a phosphatase and tensin homolog (PTEN) negative cancer in a subject in need of treatment thereof, the method comprising:
   administering to a subject diagnosed with a PTEN negative cancer a therapeutic amount of a cyclosporine, wherein the cancer is breast cancer, prostate cancer, colon cancer, glioblastoma, endometrial cancer, lung cancer, thyroid cancer, lymphomas, ovarian cancer, or a combination thereof, and whereby the cancer is treated.

5. The method of any one of claims 1-4, wherein the cyclosporine is a naturally occurring cyclosporine.

6. The method of claim 5, wherein the cyclosporine is cyclosporine A.

7. The method of any one of claims 1-4, wherein the cyclosporine is a cyclosporine derivative.

8. The method of claim 7, wherein the cyclosporine derivative is a non-immuno suppressive derivative.

9. The method of claim 7, wherein the cyclosporine derivative is the agent of Formula I, the agent of Formula II, NIM-811, SCY-635, DEBIO-025, Formula III, Formula IV, Formula V, Formula VI, Formula VII, Formula VIII, or any combination thereof.

10. The method of any one of claims 1-4, wherein the cancer is a triple negative breast cancer.

11. The method of any one of claims 1-4, wherein the cancer is a hormone negative prostate cancer.

12. The method of any one of claims 1-4, comprising administering the cyclosporine in a combination with a therapeutic amount of a poly (ADP-ribose) polymerase (PARP) inhibitor or a deoxyribonucleic acid (DNA) cross-linking agent, or a combination thereof.

13. The method of claim 12, wherein the DNA cross-linking agent is cisplatin, mitomycin C, cyclophosphamide, chlorambucil, uramustine, ifosfamide, melphalan, bendamustine, carmustine, or any combination thereof.

14. The method of claim 12, wherein the PARD inhibitor is olaparib.

15. The method of claim 9, wherein the cyclosporine derivative is the agent of Formula VI.

* * * * *